US011663276B1

(12) United States Patent
Spector et al.

(10) Patent No.: US 11,663,276 B1
(45) Date of Patent: May 30, 2023

(54) SYSTEMS AND METHODS FOR GENERATING HYPERMEDIA-BASED GRAPHICAL USER INTERFACES FOR MOBILE DEVICES

(71) Applicant: TeleTracking Technologies, Inc., Pittsburgh, PA (US)

(72) Inventors: Jason A. Spector, Pittsburgh, PA (US); Shawn M. Melvin, Pittsburgh, PA (US)

(73) Assignee: TeleTracking Technologies, Inc., Pittsburgh, PA (US)

(*) Notice: Subject to any disclaimer, the term of this patent is extended or adjusted under 35 U.S.C. 154(b) by 0 days.

(21) Appl. No.: 17/477,824

(22) Filed: Sep. 17, 2021

Related U.S. Application Data

(63) Continuation of application No. 16/843,969, filed on Apr. 9, 2020, now Pat. No. 11,151,201, which is a
(Continued)

(51) Int. Cl.
*G06F 16/30* (2019.01)
*G06F 16/93* (2019.01)
(Continued)

(52) U.S. Cl.
CPC .............. *G06F 16/94* (2019.01); *G06F 3/048* (2013.01); *G06F 21/6245* (2013.01);
(Continued)

(58) Field of Classification Search
CPC ...... G06F 16/94; G06F 3/048; G06F 21/6245; G16H 10/60; G16H 40/20; G16H 40/60
See application file for complete search history.

(56) References Cited

U.S. PATENT DOCUMENTS 10,171,935 B1   1/2019  Reyes et al.
2009/0033633 A1* 2/2009  Newman .............. G06F 3/04883
                                                              345/173
(Continued)

FOREIGN PATENT DOCUMENTS

JP          2004265077 A  *  9/2004
WO    WO-2016025995 A1  *  2/2016  ........... G06F 19/322

OTHER PUBLICATIONS

English Translation of JP 2004265077A, by Sato, Published on Sep. 24, 2004 (Year: 2004).*
(Continued)

*Primary Examiner* — Mahesh H Dwivedi
(74) *Attorney, Agent, or Firm* — Ference & Associates LLC

(57) ABSTRACT

Systems and methods are provided for generating hypermedia-based graphical user interfaces for display on a mobile device. In one embodiment, the systems and methods may include at least one processor in communication with a mobile device associated with a user; and a storage medium storing instructions. When executed, the instructions may configure the at least one processor to automatically generate one or more queries for information identifying the user and an individual associated with the user, automatically generate one or more requests for status information and real-time location information for the individual, automatically generate, based on the requested status information and real-time location information, a plurality of hypermedia elements for a graphical user interface being formatted for the mobile device, and provide the automatically generated hypermedia elements for display in a graphical user interface formatted for the mobile device.

17 Claims, 19 Drawing Sheets

Related U.S. Application Data continuation of application No. 15/853,637, filed on Dec. 22, 2017, now Pat. No. 10,650,061.

(60) Provisional application No. 62/438,748, filed on Dec. 23, 2016.

(51) Int. Cl.
*G16H 10/60* (2018.01)
*G16H 40/20* (2018.01)
*G16H 40/60* (2018.01)
*G06F 3/048* (2013.01)
*G06F 21/62* (2013.01)

(52) U.S. Cl.
CPC ............ *G16H 10/60* (2018.01); *G16H 40/20* (2018.01); *G16H 40/60* (2018.01)

(56) References Cited

U.S. PATENT DOCUMENTS

| | | | |
|---|---|---|---|
| 2009/0315735 A1 | 12/2009 | Bhavani et al. | |
| 2009/0319298 A1* | 12/2009 | Weiss | G16H 80/00 707/999.107 |
| 2012/0136221 A1* | 5/2012 | Killen | G16H 40/67 600/300 |
| 2012/0179490 A1 | 7/2012 | Fuhrmann et al. | |
| 2014/0222446 A1 | 8/2014 | Ash et al. | |
| 2014/0278548 A1 | 9/2014 | Munro et al. | |
| 2015/0012887 A1* | 1/2015 | Ash | G16H 15/00 715/835 |
| 2015/0019642 A1 | 1/2015 | Wang et al. | |
| 2015/0066648 A1 | 3/2015 | Kane, Jr. et al. | |
| 2015/0112717 A1 | 4/2015 | Saleh et al. | |
| 2015/0213195 A1 | 7/2015 | Blechman et al. | |
| 2015/0213223 A1 | 7/2015 | Amarasingham et al. | |
| 2015/0213224 A1 | 7/2015 | Amarasingham et al. | |
| 2015/0310659 A1 | 10/2015 | Spear et al. | |
| 2015/0356249 A1 | 12/2015 | Wright et al. | |
| 2017/0068785 A1* | 3/2017 | Experton | H04W 12/02 |
| 2017/0116381 A1 | 4/2017 | Melvin et al. | |
| 2017/0308648 A1* | 10/2017 | Clarke | G16H 10/60 |
| 2017/0364653 A1 | 12/2017 | Wong et al. | |
| 2019/0108909 A1 | 4/2019 | Lee et al. | |

OTHER PUBLICATIONS

Article entitled "EASE app updates families on patients' progress during surgery", by Mathias, dated Feb. 2015 (Year: 2015).*

Article entitled "Secure Apps loop in Families During Surgeries", by OR Manager, dated Jul. 16, 2016 (Year: 2016).*

* cited by examiner

SYSTEMS AND METHODS FOR GENERATING HYPERMEDIA-BASED GRAPHICAL USER INTERFACES FOR MOBILE DEVICES

CROSS REFERENCE TO RELATED APPLICATIONS

This application claims priority to co-pending U.S. patent application Ser. No. 16/843,969, filed on Apr. 9, 2020, titled "Systems and Methods for Generating Hypermedia-Based Graphical User Interfaces for Mobile Devices," which claims priority to U.S. patent application Ser. No. 15/853,637, filed on Dec. 22, 2017, now U.S. Pat. No. 10,650,061, granted on May 12, 2020, titled "Systems and Methods for Generating Hypermedia-Based Graphical User Interfaces for Mobile Devices," which claims priority to U.S. Provisional Application Ser. No. 62/438,748, filed on Dec. 23, 2016, titled "Systems and Methods for Generating Hypermedia-Based Graphical User Interfaces for Mobile Devices," the contents of all of which are incorporated by reference herein.

TECHNICAL FIELD

The present disclosure is directed to the technical field of graphical user interfaces. More particularly, disclosed embodiments are directed to interactive hypermedia graphical user interfaces for mobile devices.

BACKGROUND

Modern computing systems are capable of aggregating and providing information from multiple data sources at breakneck speeds and volumes. For example, devices connected to a network can display multiple types of content such as graphics, audio, video, plain text and/or hyperlinked text.

As the amount of available information continues to increase, so too do the size and complexity of graphical user interfaces needed for displaying all of the available information. The environments and scenarios in which abundant information is available also continue to increase, yielding opportunities for technological expansion and advancement in new areas. For example, modern health care facilities and hospitals now have computerized systems that continuously generate data about patient status, patient locations, care itineraries, and scheduling for tests and discharge. Often times, friends and relatives visiting the patients are confined to waiting areas, without knowing where the patient is or when they will return to their room. Even nurses or waiting room attendants may not know the patient's status or other helpful information about the patient, and therefore speaking with facility employees is often ineffective or inaccurate. Although modern computer systems in the care facility have the capability of generating and providing status information, they are restricted from providing information to the general public due to privacy laws, and traditional user interfaces are unable to effectively provide such large amounts of patient data in a manner that can be easily understood by untrained relatives of the patients. Therefore current systems that may exist for displaying such information are insufficient for providing real-time accurate data, and lack the functionality to harness the capabilities of data available in today's technological environment.

In view of the foregoing, improved systems and methods for generation of GUIs are presented.

SUMMARY

Disclosed embodiments provide improvements in hypermedia-based graphical user interface generation. In some embodiments, database indexing is employed to automatically create requests to effectively retrieve selected information as a response to user generated queries. The disclosed embodiments may also provide mechanisms for hypermedia GUI generation, data compilation, and rendering. In some embodiments, a method is provided for creating hypermedia elements that are transferred to a mobile device in order to automatically generate an interactive graphical user interface. In other embodiments, a system is provided to broadcast hypermedia elements to authorized devices connected to a network in order to display digital content.

In some embodiments, the system is configured to handle hypermedia elements generated by different parties, and incorporate the hypermedia elements into a graphical user interface. For example, systems and methods may enable communication between hypermedia element generators to minimize redundancy and improve transfer efficiency. Indeed, the ubiquitous adoption of mobile devices exacerbates the necessity for improved systems and methods to generate GUIs based on hypermedia elements. With limited display area and bandwidth, mobile devices demand robust methods that enable the effective compilation and processing of data. Additionally, disclosed embodiments also provide hyperlinked GUIs with seamless connectivity to other mobile devices, enhanced communication security, and increased automation to minimize user interaction complexity.

Consistent with the disclosed embodiments, a computerized system for generating hypermedia-based graphical user interfaces for mobile devices is disclosed. The system may comprise at least one processor in communication with a mobile device associated with a user, and a storage medium storing instructions. When executed, the stored instructions may configure the at least one processor to automatically generate one or more queries to receive information identifying the user and an individual associated with the user, automatically generate one or more requests for status information and real-time location information for the individual, automatically generate, based on the requested status information and real-time location information, hypermedia elements, the graphical user interface being formatted for the mobile device, and provide the automatically generated hypermedia elements for display in a graphical user interface formatted for the mobile device.

Consistent with the disclosed embodiments, a computerized method for generating hypermedia-based graphical user interfaces for display on a mobile device is disclosed. The computerized method may include: automatically generating one or more queries for information identifying the user and an individual associated with the user, automatically generating one or more requests for status information and real-time location information for the individual, automatically generating, based on the requested status information and real-time location information, a plurality of hypermedia elements for a graphical user interface being formatted for the mobile device, and providing the automatically generated hypermedia elements for display in a graphical user interface formatted for the mobile device.

Consistent with yet other disclosed embodiments, a non-transitory computer-readable medium storing instructions which, when executed, cause one or more processors to perform a computerized method for generating hypermedia-based graphical user interfaces is disclosed.

The foregoing general description and the following detailed description are exemplary and explanatory only and are not restrictive of the claims.

BRIEF DESCRIPTION OF THE DRAWINGS

The accompanying drawings, which are incorporated in and constitute a part of this specification, illustrate several embodiments and, together with the description, serve to explain the disclosed principles. In the drawings.

DETAILED DESCRIPTION OF EXEMPLARY EMBODIMENTS

Reference will now be made in detail to exemplary embodiments, examples of which are illustrated in the accompanying drawing and disclosed herein. Wherever convenient, the same reference numbers will be used throughout the drawings to refer to the same or like parts.

Figure 1:
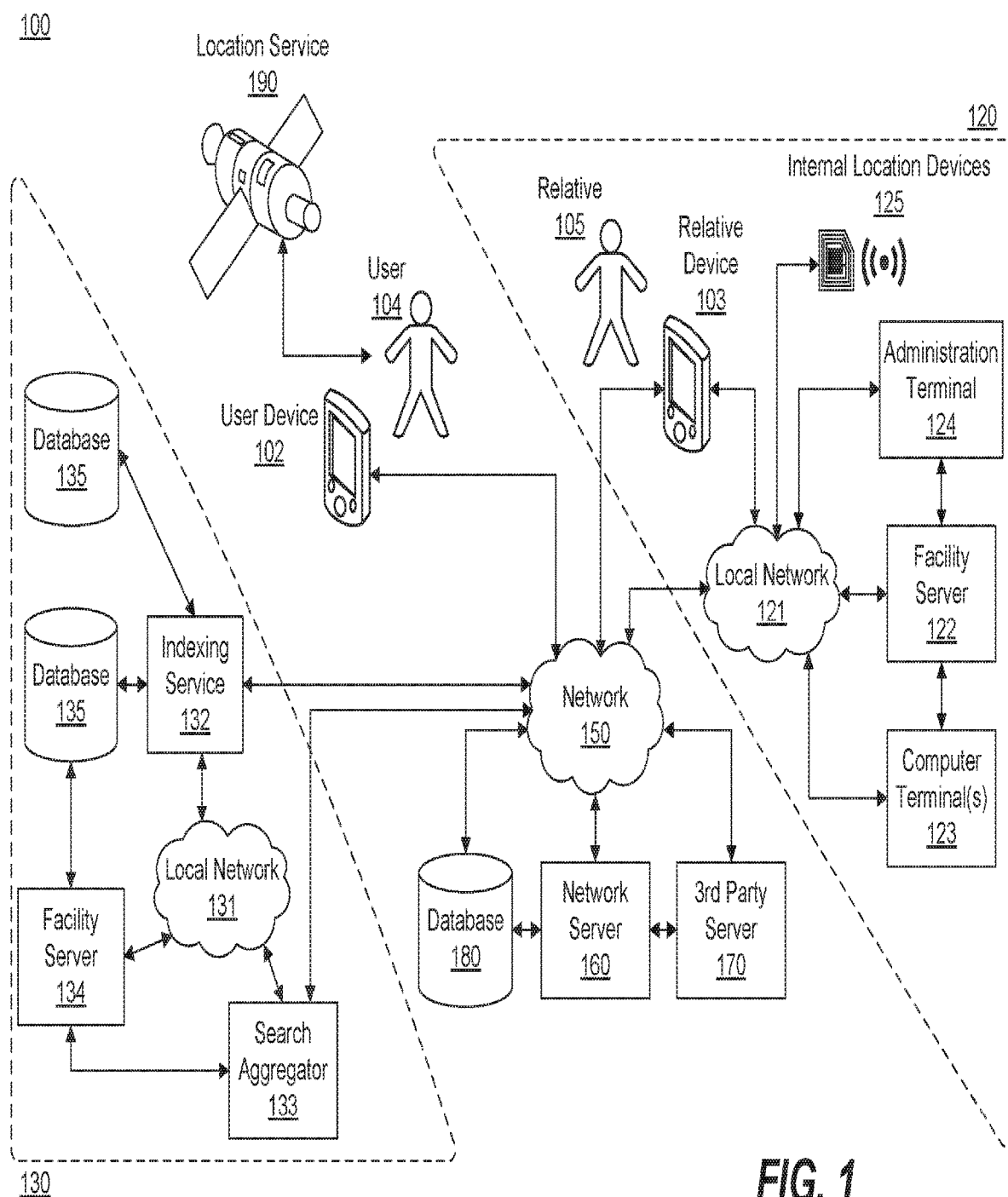
FIG. 1 shows a diagram of a computer system 100 that may be configured to perform one or more software processes that, when executed by one or more processors, perform methods consistent with disclosed embodiments.

FIG. 1 shows a diagram of a computer system 100 that may be configured to perform one or more software processes that, when executed by one or more processors, perform methods consistent with disclosed embodiments. The components and arrangements shown in FIG. 1 are not intended to limit the disclosed embodiments, as the components used to implement the disclosed processes and features may vary.

As shown in FIG. 1, system 100 may include facility system 120, hypermedia provider 130, and other external components. Facility system 120 may include facility server 122, computer terminal 123, administration terminal 124, relative device 103, and internal location devices 125. Elements in facility system 120 may communicate through local network 121. Hypermedia provider 130 may include indexing service 132, search aggregator 133, hypermedia server 134, and databases 135. Elements in hypermedia provider 130 may be connected through local network 131. Additionally, system 100 may also include components external to the facility system 120 and hypermedia provider 130. For example, system 100 may include network server 160, third party server 170, external database 180, and location service 190. External elements may communicate with facility system 120 or hypermedia provider 130 directly, through network 150, through local networks 121 and 131, or through a combination of communications methods.

Facility system 120 and hypermedia provider 130 are displayed as separated entities in FIG. 1 but they may share components and/or may be the same entity with added components. For example, a single server may function as hypermedia server 134 and facility server 122. Similarly, indexing service 132 and administration terminal 124 may share a single machine. Other combinations of elements may be also conceived. Additionally, components in system 100 may be virtually or physically defined. For example, databases 135 may be different data centers or a single data center partitioned in multiple segments. Further, computer terminal 123 and administration terminal 124 may be two independent machines or a single machine with virtual or emulated partitions.

Facility system 120 and hypermedia provider 130 may be in different physical locations or the same physical location. In some embodiments, local network 121, facility server 122, computer terminal 123, administration terminal 124, and patient device 103 may be physically disposed within a facility such as a hospital or office building (i.e. as facility system 120) while hypermedia provider 130 may be external to the facility and be located in a different location such as a dedicated data center. However, in other embodiments, facility system 120 and hypermedia provider 130 may be located in the same facility. For example, they may be both located within an office building and share local networks 121 and 131.

In some embodiments, components in facility system 120 and hypermedia provider 130 may connect to user device 102, network 150, network server 160, third party server 170, database 180, and location service 190. These elements may be external to the other facilities, may be contained in a single facility, or may be in a combination of facilities. Other components known to one of ordinary skill in the art may be included in system 100 to perform tasks consistent with the disclosed embodiments. For example, in some embodiments, facility system 120 may include one or more sensor devices such as sensors located throughout the facility to monitor one or more conditions such as occupancy, temperature, humidity, proximity, and other parameters indicative of a status or condition of a room, area, equipment, or supplies.

Computer terminal 123 may be a standalone device disposed in an office, a room, an employee station, or an alternative central location in a workplace. In some embodiments, computer terminal 123 may be a desktop or notebook computer, a flat panel or projected display, touch screen monitor, or any other display. In some embodiments, computer terminal 123 may be associated with a particular room in a facility, such as a particular patient room, hotel room, conference room, or any other type of room. Thus, a message or task request received from a computer terminal 123 may automatically associate the task request or message with the room in which computer terminal 123 is installed.

Administration terminal 124 may include a computer system or device associated with a user 104 that manages or oversees a portion of facility system 120. For example, administration terminal 124 may comprise a computer system located at a head nurse station, a housekeeping manager's office, or any other department manager's office or station.

User 104 may include one or more individuals who have an authorization to access information through system 100 about relative 105. User 104 may include relatives, friends, or any other professional that may have authorization to access information about relative 105. In some embodiments, User 104 may gain access with a password to the system. In some other embodiments, user 104 may be registered in a list of authorized users. In yet other embodiments, user 104 may gain authorized access after relative 105 responds to a request generated by facility server 122. Other authentication methods to access relative 105 information, which are compliant to Health Insurance Portability and Accountability Act (HIPAA) regulations, may also be utilized to have user 104 connected to system 100.

Relative 105 may be an individual with a relationship with facility system 120. For example, relative 105 may be an employee in a workplace environment such as a physician, nurse, technician, supervisor, manager, support personnel, dispatcher, or any other individual involved with facility system 120. Relative 105 may also be a patient or a visitor in facility system 120. Relative 105 may operate relative device 103, and/or another computer (not shown) to interact with system 100. System 100 may include multiple types of users such as, for example, relatives to a patient, patients, caregivers, technicians, task requestors, receptionists, and responders.

User device 102 and relative device 103 may be a personal computing device such as, for example, a general purpose or notebook computer, a mobile device with computing ability, a tablet, smartphone, wearable device such as Google Glass™ or smart watches, or any combination of these computers and/or affiliated components. In some embodiments, user device 102 and relative device 103 may be a computer system or mobile computer device that is operated by user 104 and patient 105 respectively. In some embodiments, user device 102 may be associated with a particular individual such as user 104, such that authentication services correlate devices and users.

In some embodiments, user device 102 may communicate with facility server 122 and/or administration terminal 124 via direct wireless communication links (not shown), or via a combination of one or more of local network 121 and/or network 150.

In some embodiments, one or more individuals such as patients or member of the public may send and receive information to facility system 120. In the example shown in FIG. 1, user 104 may access information of relative 105 through network 150.

Facility server 122 may be operated by a facility such as a hospital, business, retail location, and the like. Facility server 122 may also be operated by a contractor and/or a software service provider. Facility server 122 may enable communication within a computer-based system including computer system components such as desktop computers, workstations, tablets, hand held computing devices, memory devices, and/or internal network(s) connecting the components.

Network 150 may comprise any type of computer networking arrangement used to exchange data. For example, network 150 may be the Internet, a private data network, virtual private network using a public network, and/or other suitable connection(s) that enables system 100 to send and receive information between the components of system 100. Network 150 may also include a public switched telephone network ("PSTN") and/or a wireless cellular network.

Local networks 121 and 131 may comprise any type of computer networking arrangement used to exchange data in a localized area, such as WiFi, Bluetooth™, Ethernet, and other suitable short-range connections that enable computer terminal 123, facility server 122, hypermedia server 134, indexing service 132, search aggregator 133, and user device 102, to send and receive information between the components of system 100. In some embodiments, local networks 121 and 131 may be excluded, and connected elements may communicate with system 100 components via network 150. In some embodiments, connected components may communicate with one or more system 100 components via a direct wired or wireless connection. In some embodiments, local networks 121 and 131 may comprise a portion of network 150 or an extension of network 150.

Network server 160, third party server 170, and database 180 may be one or more servers or storage services provided by an entity such as a provider of networking, cloud, or backup services. For example, in some embodiments, network server 160 may be associated with a cloud computing service such as Microsoft Azure™ or Amazon Web Services™. In such embodiments, network server 160 may comprise a plurality of geographically distributed computing systems executing software for performing one or more functions of the disclosed methods. Additionally, in some embodiments, third party server 170 may be associated with a messaging service, such as, for example, Apple Push Notification Service, Azure Mobile Services, or Google Cloud Messaging. In such embodiments, third party server 170 may handle the delivery of messages and notifications related to functions of the disclosed embodiments, such as task creation, task assignment, task alerts, and task completion messages and notifications.

Indexing service 132, may be a component configured to provide a plurality of pointers, each pointing, for example, to a storage location for a certain type of relevant information in one of the databases 135. When extracting information, an element in system 100 and connected to network 150 may, for example, look up one or more pointers associated with the desired information type in the index server 132 and may follow the pointer to extract the desired information from the indicated location in databases 135. In some embodiments, the index server 132 may dynamically update the various pointers to reflect, for example, changes in storage format and/or location in the relevant databases.

In some embodiments, the indexing service 132 may additionally store some extracted information, for example, to enable quick access to that information at a later time.

Search aggregator 133 may include a memory device collect search results. As elements in system 100 connected to network 150 generate queries to the multiple databases, search aggregator 133 may receive and store the generated results. Once a search processing is complete, search aggregator 133 may forward the total results to application a server such as indexing service 132 or facility server 122. For example, search aggregator 133 may serve as a local cache of results to provide complete results in a single transmission anytime data bases 135 are queried. Search aggregator 133 may apply a format to the documents based on the particular search or the device from which the query was generated.

In some embodiments, system 100 may include configurations that vary from the example shown in FIG. 1, which illustrates a facility system 120 and hypermedia provider 130 working in concert with a cloud computing system including network server 160, third party server 170, and database 180. As a first variation, system 100 may include only facility system 120, and thus may exclude cloud computing components such as network server 160, third party server 170, and database 180. In such embodiments, facility system 120 may handle substantially all operations and functions of the present embodiments. As a second variation, system 100 may exclude components of facility system 120 and/or hypermedia provider 130. For example, facility server 122 and hypermedia server 134, may be excluded from system 100. In such embodiments, a cloud computing system including network server 160, third party server 170, and/or database 180 may handle some or all computing and message-related functions of the disclosed embodiments. Alternatively or additionally, components may be merged. For example, databases 135 may be included in hypermedia server 134.

Figure 2:
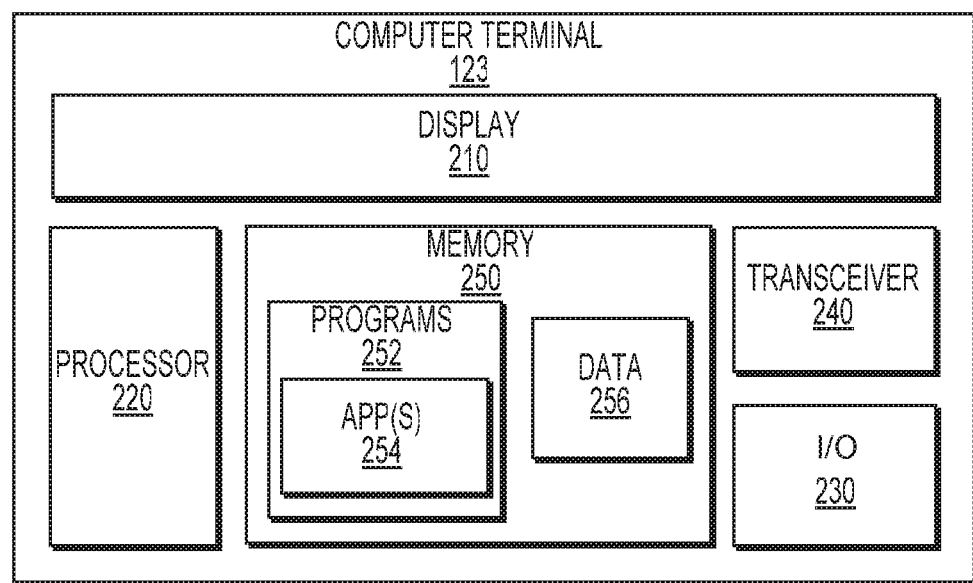
FIG. 2 shows a diagram of computer terminal 123, consistent with disclosed embodiments.

FIG. 2 shows a diagram of computer terminal 123, consistent with disclosed embodiments. As shown, computer terminal 123 may include a display 210, one or more processors 220, input/output ("I/O") devices 230, a transceiver 240, and memory 250.

Display 210 may include one or more screens for displaying task management information such as, for example, liquid crystal display (LCD), plasma, cathode ray tube (CRT), or projected screens.

Processor 220 may be one or more known processing devices, such as microprocessors manufactured by Intel™ or AMD™ or licensed by ARM. Processor 220 may constitute a single core or multiple core processors that executes parallel processes simultaneously. For example, processor 220 may be a single core processor configured with virtual processing technologies. In certain embodiments, processor 220 may use logical processors to simultaneously execute and control multiple processes. Processor 220 may implement virtual machine technologies, or other known technologies to provide the ability to execute, control, run, manipulate, store, etc. multiple software processes, applications, programs, etc. In another embodiment, processor 220 may include a multiple-core processor arrangement (e.g., dual, quad core, etc.) configured to provide parallel processing functionalities to allow computer terminal 123 to execute multiple processes simultaneously. One of ordinary skill in the art would understand that other types of processor arrangements could be implemented that provide for the capabilities disclosed herein.

I/O devices 230 may include one or more devices that allow computer terminal 140 to receive input from a user. I/O devices 230 may include, for example, one or more pointing devices, keyboards, buttons, switches, touchscreen panels, cameras, barcode scanners, radio frequency identification (RFID) tag reader, and/or microphones.

Transceiver 240 may include one or more communication modules for establishing communication between computer terminal 123 and other devices of system 100 via, for example, local network 121 and/or network 150. For example, transceiver 240 may include circuitry and one or more antennas for communicating wirelessly with local network 121 using a short range/near-field wireless communication protocol such as Bluetooth™, Bluetooth™ LE, WiFi, and Zigbee. Further, transceiver 240 may communicate with network 150 and/or local network 121 using any known network protocol including any form of wired or wireless internet access.

Memory 250 may include a volatile or non-volatile, magnetic, semiconductor, solid-state, tape, optical, removable, non-removable, or other type of storage device or tangible (i.e., non-transitory) computer-readable medium that stores one or more program(s) 252, such as app(s) 254, and data 256. Data 256 may include, for example, user information, task information, and display settings and preferences. In some embodiments, data 256 may include one or more rule sets for prioritizing and assigning tasks to one or more employees.

Program(s) 252 may include operating systems (not shown) that perform known operating system functions when executed by one or more processors. By way of example, the operating systems may include Microsoft Windows™, Unix™, Linux™ Android™ and Apple™ operating systems, Personal Digital Assistant (PDA) type operating systems, such as Microsoft CE™, or other types of operating systems. Accordingly, disclosed embodiments may operate and function with computer systems running any type of operating system. Computer terminal 123 may also include communication software that, when executed by a processor, provides communications with network 150 and/or local network 121, such as Web browser software, tablet, or smart hand held device networking software, etc.

Program(s) 252 may also include app(s) 254, such as a patient itinerary creation and management app, which when executed causes computer terminal 140 to perform processes related to creating one or more patient itineraries, managing the created itineraries with real-time analysis and modification, and performing automated tasks related to the management of patient itineraries. For example, app(s) 254 may configure computer terminal 123 to generate and display one or more dynamic patient itinerary display and control interfaces, to provide a calculated itinerary for a patient, display a real-time status of the patient's progress through the itinerary, identify potential delays or complications in patient care, and provide one or more alternative itineraries to mitigate the delays or complications, receive instructions from one or more user 104. Furthermore, app(s) 254 may perform one or more automated tasks associated with the patient itinerary including, for example, generating one or more job tasks related to the patient itinerary based on the patient's status and progress, canceling and/or rescheduling one or more job tasks based on changes in the itinerary, requesting equipment or supplies associated with a task, and tracking the real-time status of all tasks related to the patient itinerary. In some embodiments, app(s) 254 may configure one or more computer systems to analyze historical patient itinerary data and hospital performance data to identify patterns, trends or correlative relationships in the historical data. For example, trends in historical data may indicate that certain patient diagnoses are associated with certain lengths of stay, or often experience delays and complications in certain portions of the itinerary. Historical data, identified trends and patterns, and correlative relationships may be identified through regression analysis, queuing analysis and other known statistical analysis methods, stored, and recalled during the creation and/or modification of new patient itineraries, to provide ever-improving patient care and efficiency. Correlations could be stored, retrieved and processed as Stochastic Information Packets (SIPs), Distribution Strings (DIST) or Stochastic Library Unit with Relationships Preserved (SLURPs). As discussed in further detail below, in some embodiments the implementation of these functions and the advantages realized by the present embodiments are attributed to the use of high-speed data and communication network, as well as personal communication and tracking devices disposed throughout a hospital.

Figure 3:
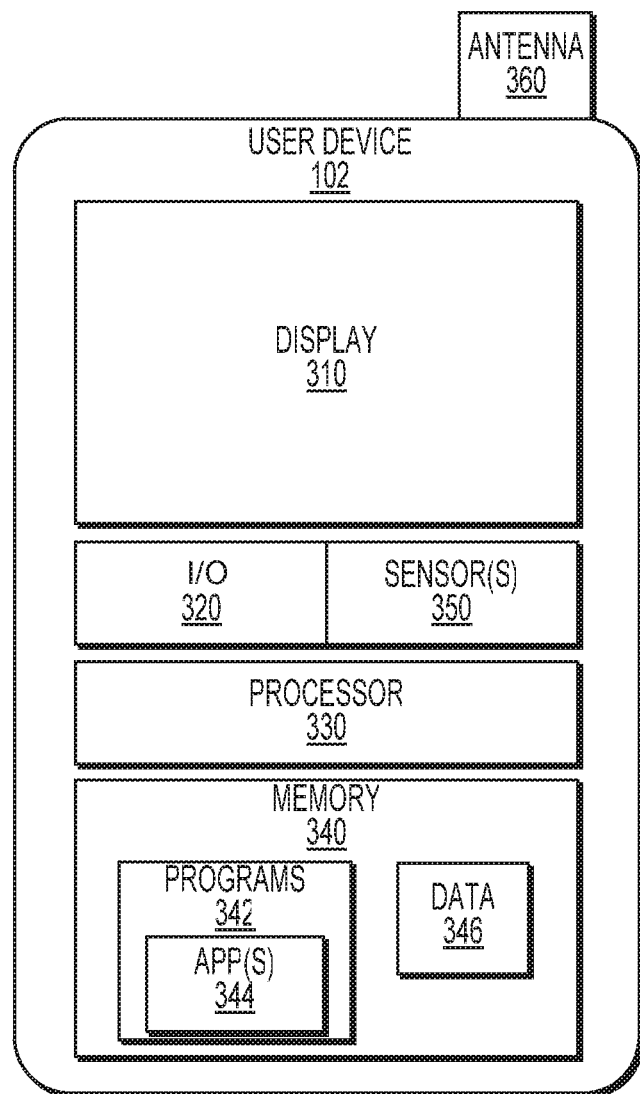
FIG. 3 shows a diagram of an exemplary user device 102, consistent with disclosed embodiments.

FIG. 3 shows a diagram of an exemplary user device 102, consistent with disclosed embodiments. As shown, user device 102 may include display 310, I/O device(s) 320, processor 330, memory 340 having stored thereon data 346 and one or more programs 342, such as app(s) 344, sensor(s) 350, and antenna 360.

Display 310 may include one or more devices for displaying information, including but not limited to, liquid crystal displays (LCD), light emitting diode (LED) screens, organic light emitting diode (OLED) screens, and other known display devices.

I/O devices 320 may include one or more devices that allow user device 102 to send and receive information. I/O devices 320 may include, for example, a pointing device, keyboard, buttons, switches, and/or a touchscreen panel. I/O devices 320 may also include one or more communication modules (not shown) for sending and receiving information via antenna 360 from other components in system 100 by, for example, establishing wired or wireless connectivity between user device 102 to local networks 121 or 131, network 150, or by establishing direct wired or wireless connections between user device 102 and other components of system 100. Direct connections may include, for example, Bluetooth™, Bluetooth LE™, WiFi, near field communications (NFC), or other known communication methods which provide a medium for transmitting data between separate devices.

Processor(s) 330 may be one or more known computing devices, such as those described with respect to processor 220 in FIG. 2.

Memory 340 may be a volatile or non-volatile, magnetic, semiconductor, tape, optical, removable, non-removable, or other type of storage device or tangible (i.e., non-transitory) computer-readable medium such as those described with respect to memory 250 in FIG. 2.

In some embodiments, user device 102 may contain one or more sensors 350 for collecting environmental, movement, location, and/or security data. Sensors 350 may include: one or more environmental sensors such as, for example, ambient light sensors, microphones, air pressure sensors, temperature sensors, and humidity sensors; motion detectors such as, for example, GPS receivers, location-based data receivers, accelerometers, and gyroscopes; and security sensors such as, for example, fingerprint readers, retina scanners, and other biometric sensors capable of use for security and individual identification. In some embodiments, processor 330 may use data collected by sensors 350 to control or modify functions of program(s) 342.

Figure 4:
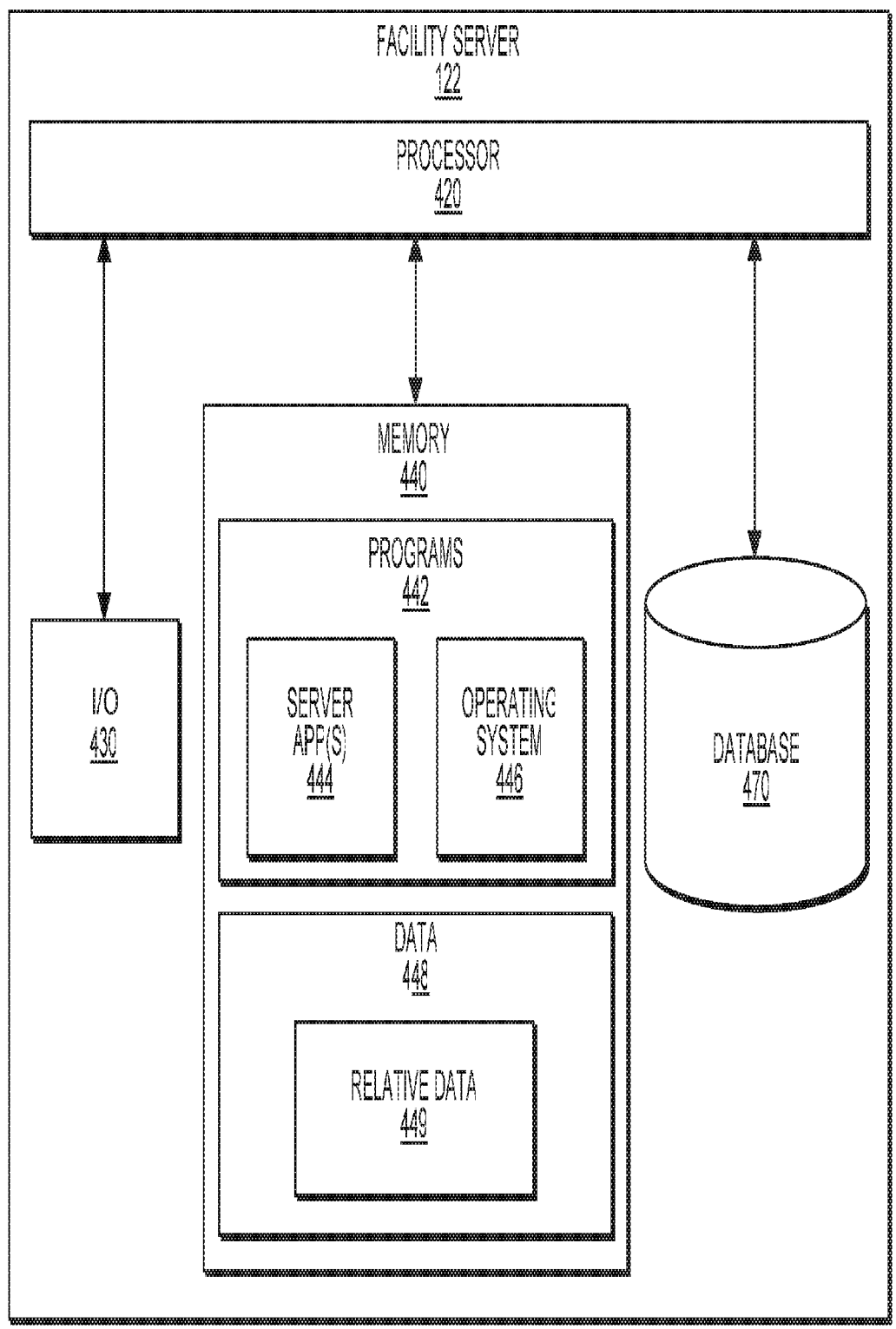
FIG. 4 shows a diagram of an exemplary facility server 122, consistent with disclosed embodiments.

FIG. 4 shows a diagram of an exemplary facility server 122, consistent with disclosed embodiments. In some embodiments, facility server 122 may support or provide a cloud computing service, such as Microsoft Azure™ or Amazon Web Services™. In such embodiments, facility server 122 may include one or more distributed computer systems capable of performing distributed computing functions and providing cloud computing services and functions consistent with disclosed embodiments. In some embodiments, facility server 122 may operate in conjunction with network server 160. In other embodiments, facility server 122 may operate alone, and network server 160 may be replaced by a network connection to network 150 and/or local networks 121 and 131. In such embodiments, facility server 122 may perform all functions associated with the disclosed methods. In other embodiments, facility server 122 may operate alone, without network server 160. In such embodiments, facility system 120 may operate as a stand-alone system, in which facility server 122 performs all functions associated with the disclosed methods. Those of ordinary skill in the art will appreciate that the computing arrangements are not limited to these examples, and that other embodiments may include one or more alternate configurations of computing systems capable of performing functions associated with the disclosed embodiments.

As shown in FIG. 4, facility server 122 may include one or more processor(s) 420, input/output ("I/O") devices 430, memory 440 storing programs 442 (including, for example, server app(s) 444 and operating system 446) and data 448 (including relative data 449), and a database 470. Facility server 122 may be a single server or may be configured as a distributed computer system including multiple servers or computers that interoperate to perform one or more of the processes and functionalities associated with the disclosed embodiments.

Processor(s) 420 may be one or more known computing devices, such as those described with respect to processor 220 in FIG. 2.

In some embodiments, facility server 122 may also include one or more I/O devices 430 including interfaces for receiving signals or input from devices and providing signals or output to one or more devices that allow data to be received and/or transmitted by facility server 122. For example, facility server 122 may include interface components, which may provide interfaces to one or more input devices, such as one or more keyboards, mouse devices, and the like, that enable facility server 122 to receive input from one or more relative 105 that is associated with facility system 120.

In some embodiments, facility server 122 may include one or more storage devices configured to store information used by processor 420 (or other components) to perform certain functions related to the disclosed embodiments. In one example, facility server 122 may include memory 440 that includes instructions to enable processor 420 to execute one or more applications, such as server applications, an electronic transaction application, an account status application, network communication processes, and any other type of application or software known to be available on computer systems. Alternatively or additionally, the instructions, application programs, etc. may be stored in an internal database 470 or external database 180 (shown in FIG. 1) in communication with facility server 122, such as one or more database or memory accessible over network 150. Database 470 or other external storage may be a volatile or non-volatile, magnetic, semiconductor, tape, optical, removable, non-removable, or other type of storage device or tangible (i.e., non-transitory) computer-readable medium.

In one embodiment, facility server 122 may include memory 440 that includes instructions that, when executed by processor 420, perform one or more processes consistent with the functionalities disclosed herein. Methods, systems, and articles of manufacture consistent with disclosed embodiments are not limited to separate programs or computers configured to perform dedicated tasks. For example, facility server 122 may include memory 440 that may include one or more programs 442 to perform one or more functions of the disclosed embodiments. Moreover, processor 420 may execute one or more programs located remotely from account information display system 100. For example, facility server 122 may access one or more remote programs, that, when executed, perform functions related to disclosed embodiments.

Programs 450 stored in memory 440 and executed by processor(s) 420 may include one or more server app(s) 452 and operating system 454. Server app(s) 452 may incorporate one or more apps configured to receive input of information related to tracking patient statuses such as receiving patient attributes, diagnoses, and conditions, receiving staff schedules and staff skills, receiving one or more hospital rules and legal restrictions, receiving treatment requirements, physicians' orders and regimens associated with patient diagnoses, analyzing received data using one or more rule sets, computer models, or other processing logic, generating data associated with one or more graphical user interfaces, generating one or more communications and/or commands to other computer systems or devices such as user device 102, and updating the graphical user interfaces in real-time based on new data or changes in the analysis results.

In some embodiments, memory 440 may store data 448 including data associated with patients, staff, tasks, assets such as hospital beds, assignment and graphical user interface generation algorithms, historical data, data derived from historical data such as trends, patterns, and correlative relationships. For example, data 448 may include one or more entries including relative data 449 (e.g., identifications of relative, current status, schedules, history), medical records, assignment history, conditions, treatment plans, room assignments, room location, and legal and restrictions and regulations. Data 448 may also include information about procedures available in facility system 120. For the purpose of this application, disclosed procedures are not limited to a medical procedure and may include multiple tasks that may be performed a facility. For example, procedures may refer to medical procedures, such a blood analysis and surgical operations. However, procedures may also refer to doctor appointments, or medical tests, or scheduled activities. Additionally, procedures may also refer to facility services such as transport and/or discharge. In addition, data 448 may also include the current location of the patient, the status of each of the patient physician orders (e.g., lab orders, radiology orders), bed assignment priorities, milestones (e.g., discharge and transfer milestones), transport request status, patient hand-off during shift change, continuity of care data for resource assignments, custom patient attributes, and the real-time statuses of delays or complications in hospital departments and units. In some embodiments, data 448 is stored in database 470, memory 440, memory 250, memory 340, database 180, and any combination thereof.

In some embodiments, memory 440 and database 470 may include one or more memory devices that store data and instructions used to perform one or more features of the disclosed embodiments. Memory 440 and database 470 may also include any combination of one or more databases controlled by memory controller devices (e.g., server(s), etc.) or software, such as document management systems, Microsoft SQL databases, SharePoint databases, Oracle™ databases, Sybase™ databases, or other relational databases.

Facility server 122 may communicate with one or more remote memory devices (e.g., third party server 170 and/or database 180) through network 150 or a different network (not shown). The remote memory devices may be configured to store information and may be accessed and/or managed by network server 160. By way of example only, the remote memory devices may be document management systems, Microsoft SQL database, SharePoint databases, Oracle™ databases, Sybase™ databases, or other relational databases. Systems and methods consistent with disclosed embodiments, however, are not limited to separate databases or even to the use of a database.

Figure 5:
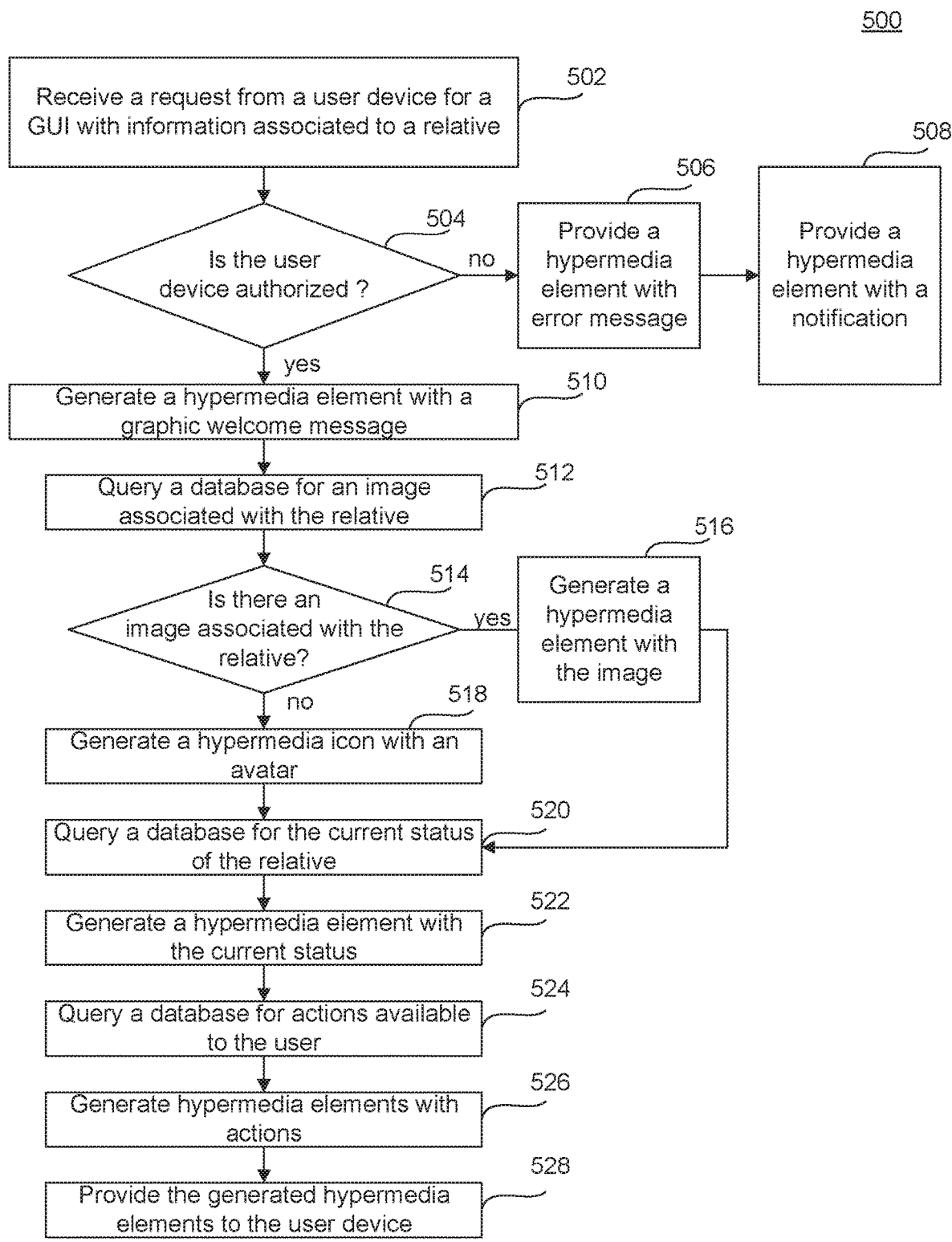
FIG. 5 depicts an example of a flowchart for providing hypermedia elements to generate a primary GUI, consistent with embodiments of the present disclosure.

FIG. 5 depicts an example of a flowchart for providing hypermedia elements to generate a primary GUI, consistent with embodiments of the present disclosure. Facility server 122 may receive a request for information to generate a GUI from user device 102. This request may come in the form of an internet protocol message, a query data packet, or a port opening instruction. The request may include information of relative 105 such as a name and/or identification number. After reception of a request facility server 122 may determine if the user is an authorized list in step 504. In some embodiments, facility server 122 may make this determination by querying a list of authorized users and comparing the identification of user device 102 with a list of authorized users. In other embodiments, facility server 122 may reply to the request by providing data to generate a hypermedia form in user device 102 that requests and captures authentication information. In such embodiments, user 104 may transmit a password and/or keyword through the provided hypermedia in the GUI to identify itself as an authorized user. Alternative methods of identification such as voice recognition or token exchanges may also be used in step 504 to determine whether user device 102 is authorized to receive information associated with relative 105. In yet other embodiments, facility server 122 may send a request to relative device 103 to authorize user device 102. The request may include information of user device 102 and hypermedia elements to collect information.

Facility server 122 may determine that user device 102 is not authorized to receive information (step 504: no). Facility server 122 may then automatically generate and provide a hypermedia element with error message to user device 102 indicating that it is not an authorized user (step 506). The generated hypermedia data may include contact information of facility system 120 and/or instructions to gain authorization. Facility server 122 may also continue to step 508 and generate a hypermedia element with a notification that is provided to relative device 103 and/or administration terminal 124. The notification may include information associated with user device 102.

In step 504, facility server 122 may alternatively determine that user device 102 is authorized to receive information (step 504: yes). Facility server 122 may then proceed to step 510 and automatically generate a welcome hypermedia element (for instance welcome message 1412 in FIG. 14), which may include a name associated with the device. Facility server 122 may then proceed to step 512 and generate a query for an image associated with relative 105. The request may be directed for example to indexing service 132 via network 150 or local network 121. The request may also be directed to network server 160, data base 180, or any other components of system 100 that may store graphical data. As a result of the query, facility server 122 may determine that there is at least one image associated with relative 105 (step 514: yes). Facility server 122 may then automatically generate a hypermedia icon which includes the image associated with relative 105 in step 516 (for example, relative image 1416 in FIG. 14). Alternatively, facility server 122 may determine that there is no image associated with relative 105 and then automatically generate a hypermedia icon with a default image such an avatar in step 515.

Facility server 122 may then automatically generate a second query for information related to the current status of relative 105. In some embodiments, the facility server 122 may communicate with components within facility system 120, such as internal location devices 125, relative device 103, and administration terminal 124, to retrieve information related to relative 105. This information may include location, personal information, doctors' notes, scheduled procedures and services, among others. Facility server 122 may then automatically generate one or multiple hypermedia elements that reflect the retrieved status information in step 518 (For example elements in section 1420 in FIG. 14).

Subsequently, facility server 122 may query servers and/or databases, locally (i.e. database 470), or through network 150, to generate one or more search requests to retrieve information associated with actions available to user device 102. Available actions may include activities in the same location as user 104, access to documents in system 100, and/or actions associated with other users authorized to receive information of relative 105. The information retrieved in step 520 may be utilized by facility server 122 to automatically generate hypermedia elements representing actions that may be executed by user 104. For example, hypermedia elements may be "available actions" icons that allow user 104 to submit send secondary queries to facility server 122 (for example elements presented in section 1430 of FIG. 14).

In step 524, facility server 122 may provide the automatically generated hypermedia elements during process 500 to user device 102. The hypermedia elements may include rendering or displaying information. For example, the hypermedia elements may include information about color, tone, and shade. The hypermedia elements may also include parameters that may be recognized by software in user device 102 before the user interface is automatically generated. For example, hypermedia elements may include information about operative systems and/or resolution preferences in order to be displayed in the screen of user device 102.

While the exemplary process describes a sequential collection and processing of information and hypermedia elements, other configurations may be possible. For example, in some embodiments the queries and generation of hypermedia elements described in steps 512-522 may be conducted in parallel or in an aleatory order. In such embodiments facility server 122 may query simultaneously multiple databases. In addition, the exemplary process describes the generation of the different hypermedia elements that are later provided to user device 102 in a single transmission. However, other embodiments where the hypermedia elements are transmitted as soon as they are automatically generated are also possible. Facility server 122 may determine transmission processes based on communication parameters such as bandwidth or user 104 preferences. The different transmission processes may result in the generation of a primary graphical user interface like the one presented in FIG. 14, which is described later.

Figure 6:
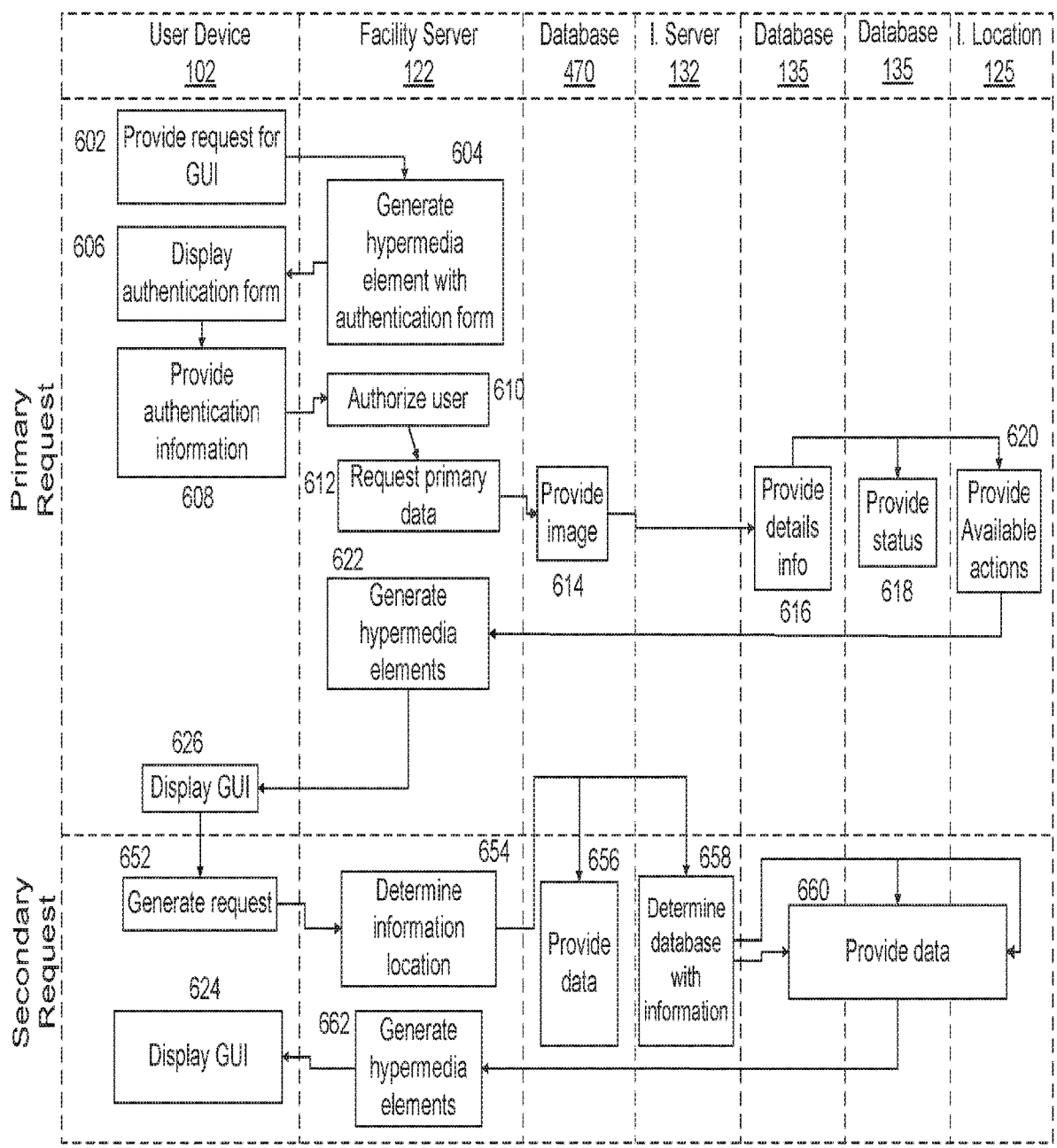
FIG. 6 is a flowchart of an exemplary process for generation and transfer of hypermedia elements, consistent with disclosed embodiments.

FIG. 6 is a flowchart of an exemplary process for generation and transfer of hypermedia elements, consistent with disclosed embodiments. Portions of the process 600 are described herein as performed by user device 102, facility server 122, database 470, indexing service 132, internal location devices 125, and databases 135. Further, the process is divided in an "Primary Request" and "Secondary Request."

Process 600 may begin with an Primary Request in step 602, in which user device 102 may provide a request for a GUI. The request may be transmitted directly to facility server 122, or may be communicated through network 150 or network 121. The request may be, for example, an internet protocol message, a query data packet, or a port opening instruction.

Upon reception of the query from user device 102, in step 604 facility server 122 may automatically generate a hypermedia element with an authentication form that is then transmitted to user device 102. In step 606, facility server 122 may display the hypermedia element with the authentication form. As a response user 104 may input the authentication information which is then provided to the facility server 122 (step 608). Authentication information may be a password, a keyword, a voice file, an image, an electronic token, or any other type of electronic file that can be used for verification purposes.

In step 610, facility server 122 may determine whether the received authentication information grants access to information of relative 105. In some embodiments, facility server 122 may make this determination by querying databases requesting approved verifications. In other embodiments, facility server 122 may use cryptography authentication methods and exchange coded messages and keys between user 104 and facility server 122 to determine access authorization. As a result of this exchange, facility server may abort the communication (step 508) or may continue with the following communication steps.

In step 612, facility server may start a hypermedia element collection routine to automatically generate the primary graphical user interface. For example, facility server 122 may follow process 500 to automatically generate interface in FIG. 14. This routine may trigger queries and responses from elements with information associated with relative 105. In some embodiments, facility server 122 may trigger a sequence of queries that are automatically generated and completed sequentially. In other embodiments, facility server 122 may automatically generate parallel sequences to the components for information associated with relative 105.

In step 614, database 470 may provide an image associated with relative 105. This image may be a registration picture acquired during registration, an image selected by relative 105, or other hypermedia element associated with relative 105. The image may in the form of a digital file such as JPEG, PNG, or TIFF JPEG.

In step, 616, database 135 may provide information about the relative 105. The information provided in step 616 may be restricted by the authorization level of user device 102. This information may include biographical data of relative 105.

In step 618, database 135 may provide the current status of relative 105, which may include a current procedure or his current location. For example, in step 618 database 135 may provide information indicating that relative 105 is currently scheduled to have an MM or that is currently in his/her room waiting for a physician visit. Information provided in step 618 may also refer to the status of relative 105 and refer to patient codes such as "Discharged to home/self care", "Transferred to an Inpatient rehabilitation facility (IRF)", or "Transferred to a critical access hospital."

In step 620, internal location devices 125 may provide information about the location of relative device 103. Facility server 122 may broadcast a query through local network 121 to internal location devices 125. As a response, internal location devices 125 may collect data of devices that are associated with relative 105. In some embodiments, internal location devices 125 may include RFID tags with dispersed readers. In other embodiments, internal location devices 125 may include distance measurement devices to anchor nodes, such as devices measuring distance to WiFi access points. In yet other embodiments, internal location devices 125 may include magnetic positioning devices, Bluetooth devices, and/or electromagnetic devices capable of determining angle and time of arrival to triangulate a signal.

In step 620, internal location devices 125 may transmit information to facility server 122, which in turn associate the received information with relative 105 to determine a location. The location is then provided to facility server 122. In some embodiments, where no location can be established through internal location devices 125, internal location devices 125 may automatically generate an error signal that alerts facility server 122 that no location could be determined.

With the provided information of multiple sources, facility server 122 may automatically generate a single or a plurality of hypermedia elements in step 622. In some embodiments, hypermedia element generation may include determining one or more graphics or text associated with a particular set of data, such as a picture representative of a type of information as indicated in a lookup table or other associative array, or using a rule set. Facility server 122 may classify the data type using known classification methods, or scan the data for metadata indicative of a datatype, and retrieve a graphic file or textual image file that corresponds with the classified type or metadata. Facility server 122 may then configure a hyperlink associated with the data. For example, facility server may identify an Internet web location or a location within one or more apps of user device 102 by scanning metadata or coding associated with the data. The identified location may be used to configure a link destination for a clickable/selectable portion of the determined graphics or text. The link destination, graphics or text, and a size or location of the clickable/selectable area may be compiled into a hypermedia element file, and stored or buffered for use in the graphical user interface.

In step 624, facility server 122 may automatically generate a graphical user interface using the automatically generated hypermedia elements and the formatting conditions specified by user device 102 in the request. For example, user device 102 may indicate the size of the screen, resolution, and navigation conditions.

In step 626, user device 102 may display the graphical user interface based on the hypermedia elements provided by the facility server 122. In alternative embodiments, user device 102 may receive the hypermedia elements and locally composed the GUI using processor 330 that may execute programs 342.

Following the initial request, described in steps 602-626, user device 102 may automatically generate Secondary Requests. For example, Secondary Requests may include opening a contact list, searching for activities, retrieving related documents or sending a message. The secondary requests may be automatically generated by interacting with elements in the GUI. For example, secondary request may be automatically generated by clicking an icon.

In step 652, user device 102 may automatically generate a secondary request by providing an internet protocol message, a query data packet, or a port opening instruction to facility server 122. As a response, in step 654 facility server 122 may determine whether the information is locally or externally stored. This determination may be based on a query to database 470 and/or information in memory 440.

In step 656, database 470 may provide any information requested which is locally store. Alternatively or additionally, in step 658 indexing service 132 may determine the location of the requested information stored in hypermedia provider 130, or in a component accessible through network 150.

In step 660, indexing service 132 may direct the query to the adequate database or service, which in turn will provide the requested information to facility server 122 or through indexing service (not shown).

Information from database 470 and/or indexed via indexing service 132 may be then provided to facility server 122. Facility server 122 may then automatically generate at least one hypermedia element in step 662, which is then utilized to automatically generate a GUI that is transmitted to the user device. In step 664, user device 102 displays a GUI using the hypermedia elements automatically generated by facility server 122.

Figure 7:
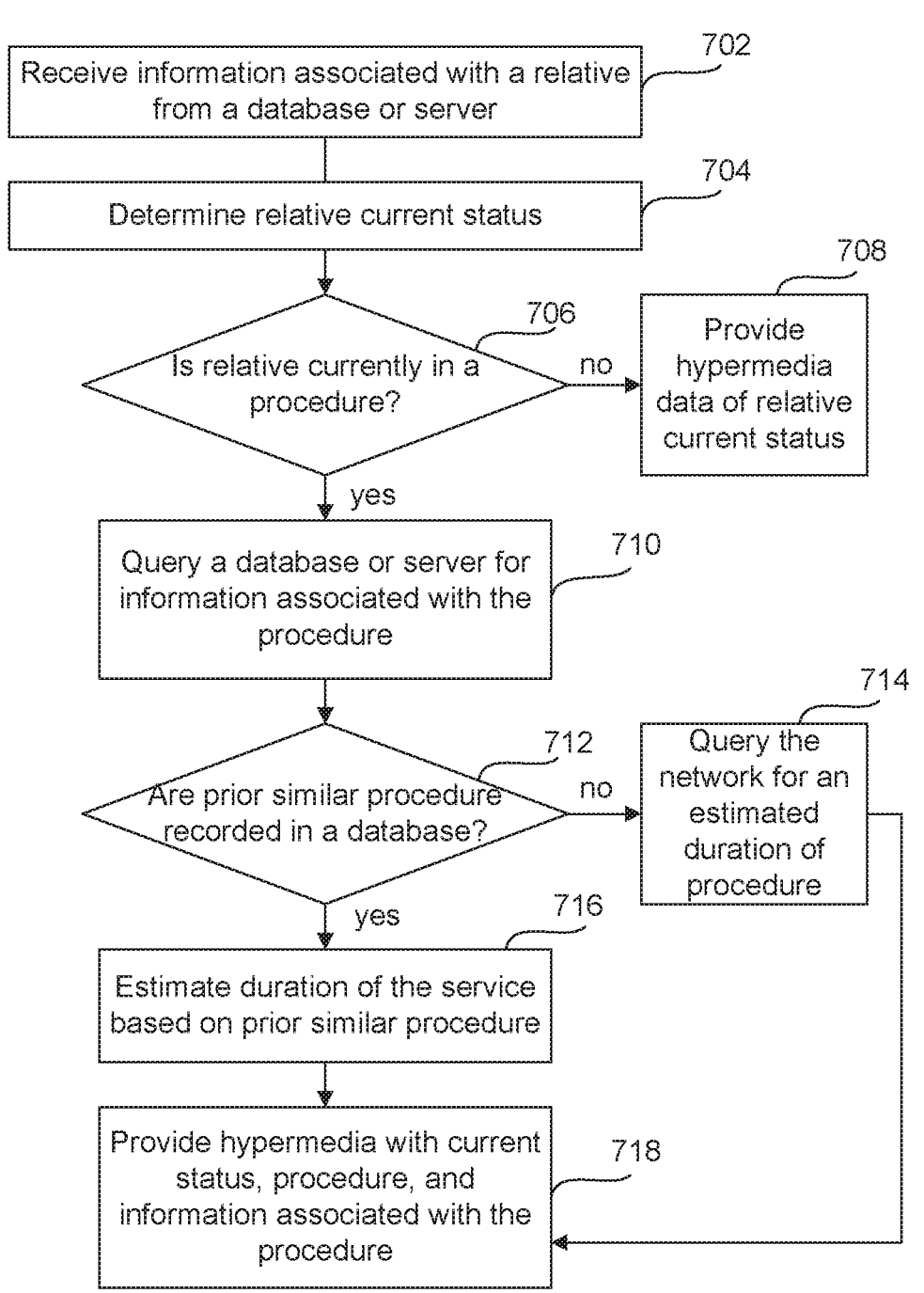
FIG. 7 is a flowchart of an exemplary process for providing hypermedia data with a current status.

FIG. 7 is a flowchart of an exemplary process for providing hypermedia elements with a current status. As a response to instructions of step 522, process 700 may start with facility server 122 receiving and compiling information of relative 105. Facility server 122 may proceed to step 704, in which it may determine current status of relative 105 based on the information received from a database, see for example step 520.

In step 706, facility server 122 may determine that the relative is not in a current procedure (step 706: no) and proceed to step 708. In step 708, facility sever 122 may automatically generate and provide a hypermedia element with only current status information. Alternatively, in step 706, facility server 122 may determine that relative 105 is currently in a procedure and proceed to step 710.

In step 710, facility server 122 may automatically generate a new query to one of the databases (470, 135, and/or 180), for more information related to the procedure identified for relative 105.

In step 712, facility server may determine if there are similar procedures recorded in a database. When facility server 122 determines that there is no record of similar procedures (step 712: no), it may then continue to step 714. In step 714, facility server 122 may automatically generate a broadcast query for time estimates of the duration of the procedure. Alternatively, facility server 122 may determine that there are local records of similar procedures (step 712: yes) and estimate the duration of the procedure for relative 105 in step 716. In step 718, facility server 122 automatically generates and provides a hypermedia element with the relative current status, procedure identification, and also additional information associated with the procedure such as typical outcomes, expected time of recovery among others.

Figure 8:
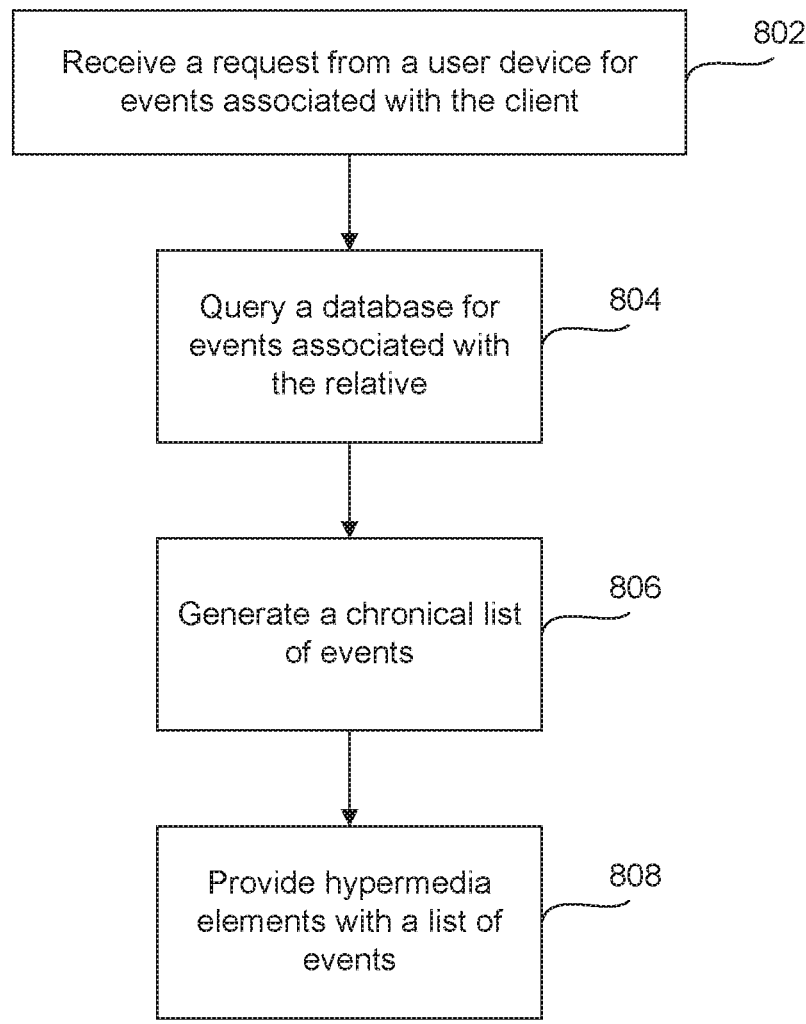
FIG. 8 is a flowchart of an exemplary process for providing hypermedia elements with associated events.

FIG. 8 is a flowchart of an exemplary process for providing hypermedia elements with associated events. In step 802, facility server may receive a secondary request for events associated with the status of relative 105. These events may include for example previous procedures, scheduled procedures, transfers, and/or notes into the record. As a response, facility server 122 may automatically generate queries to collect information of events associated with relative in step 804. For example, facility server 122 may locally query database 470 and/or query databases 180 and 135 via network 150.

In step 806, facility server 122 may compile and organize the collected information of events and automatically generate a chronological list of events. In step 808, facility server 122 may automatically generate a hypermedia element with the list of events associated with relative 105.

Figure 9:
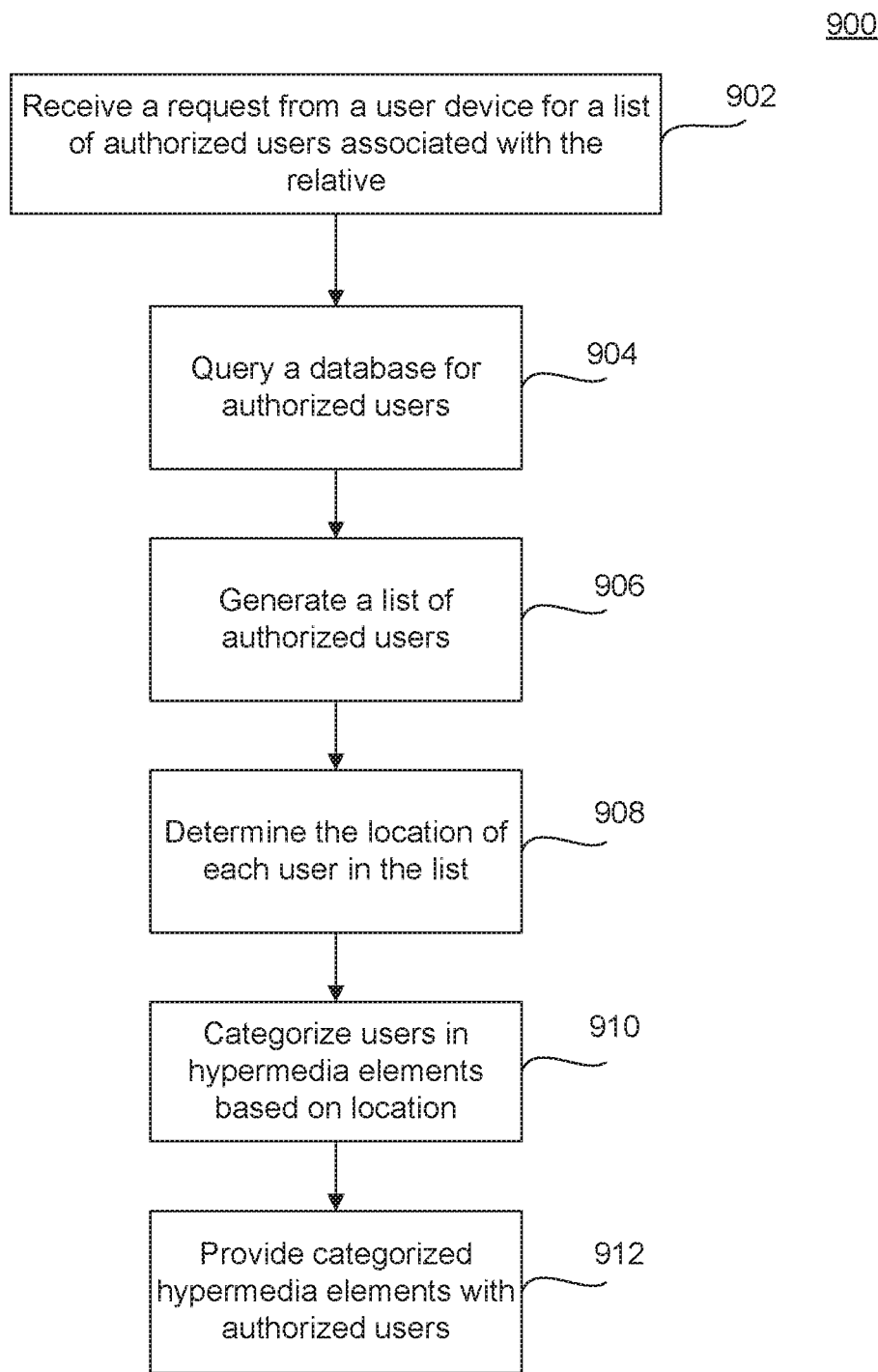
FIG. 9 is a flowchart of an exemplary process for providing hypermedia elements associated with authorized users.

FIG. 9 is a flowchart of an exemplary process for providing hypermedia elements associated with authorized users. In step 902, facility server 122 may receive a request form a user device 102 for a hypermedia element with a list of authorized users associated with relative 105. As a response, facility server 122 may query local and external databases for information of authorized users associated with relative 105. In step 906, facility server 122 may compile collected information and automatically generate a list of authorized users.

In step 908, facility server may determine the location of each user in the automatically generated list. Facility server 122 may then proceed to step 910, in which it may categorize users in list based on location. Location may be determined based on information from the location service 190, a variable selected from the user, or other localization means. For example, user 104 may indicate its location when arriving to the facility by messaging administration terminal 124. Facility server 122 then may obtain location information from administration terminal 124. Alternatively, user device 102 may be connected to location service 190 which periodically updates the location of user 104.

In step 912, facility server 122 may automatically generate a hypermedia element with the list of categorized authorized users. The list may be a single hypermedia element but may also be a plurality of hypermedia elements (for example one for each authorized user).

Figure 10:
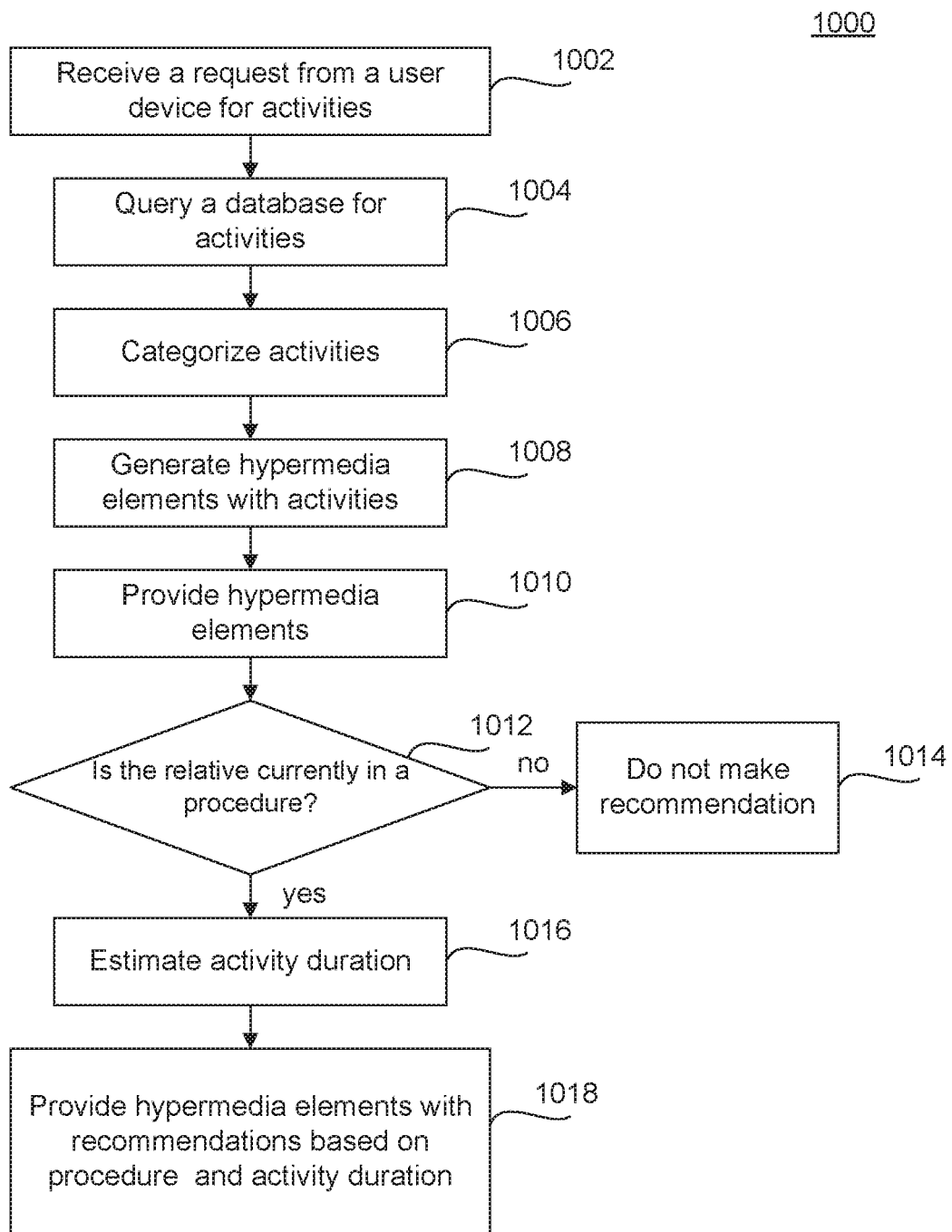
FIG. 10 is a flowchart of an exemplary process for providing hypermedia data with activities and recommendations.

FIG. 10 is a flowchart of an exemplary process for providing hypermedia data with activities and recommendations. In step 1002, facility server 122 may receive a request from user device 102 for activities and recommendations. As a response, facility server 122 may query local and external databases for activities in step 1004.

Facility server 122 may then categorize activities based on the information associated with each activity. For example, facility server 122 may categorize activities based on distance, cost, and/or estimated time. Facility server 122 may also categorize activities based on the kind of activity, creating for example independent groups for "Food and Dinning" and "Entertainment" activities.

In step 1008, facility server 122 may automatically generate hypermedia elements associated with the categorized activities. Facility server 122 may automatically generate independent hypermedia elements for each activity, each category, or group all activities in a single object. Facility server 122 may then proceed to step 1010, in which it automatically generates a GUI based on the automatically generated hypermedia element(s), which is then provided to user device 102.

Facility server 122 may then continue to step 1012 and determine if relative 105 is currently in a procedure. It may do so based on information collected in step 520 and/or location information provided by internal location devices 125. When facility server 122 determines that relative 105 is not in a procedure (step 1011: no), it may proceed to step 1014 and finalize the process without providing any recommendation. On the other hand, if facility server 122 determines that relative 105 is currently in a procedure (step 1012: yes), it may proceed to estimate the current procedure duration, with process like the ones described in steps 712-716, estimate duration of activities in the list (step 1016), and provide a recommendation based on the procedure duration and estimated activity duration (step 1018). Recommendations provided in step 1018 may also be based on user 104 location and/or preferences.

Figure 11:
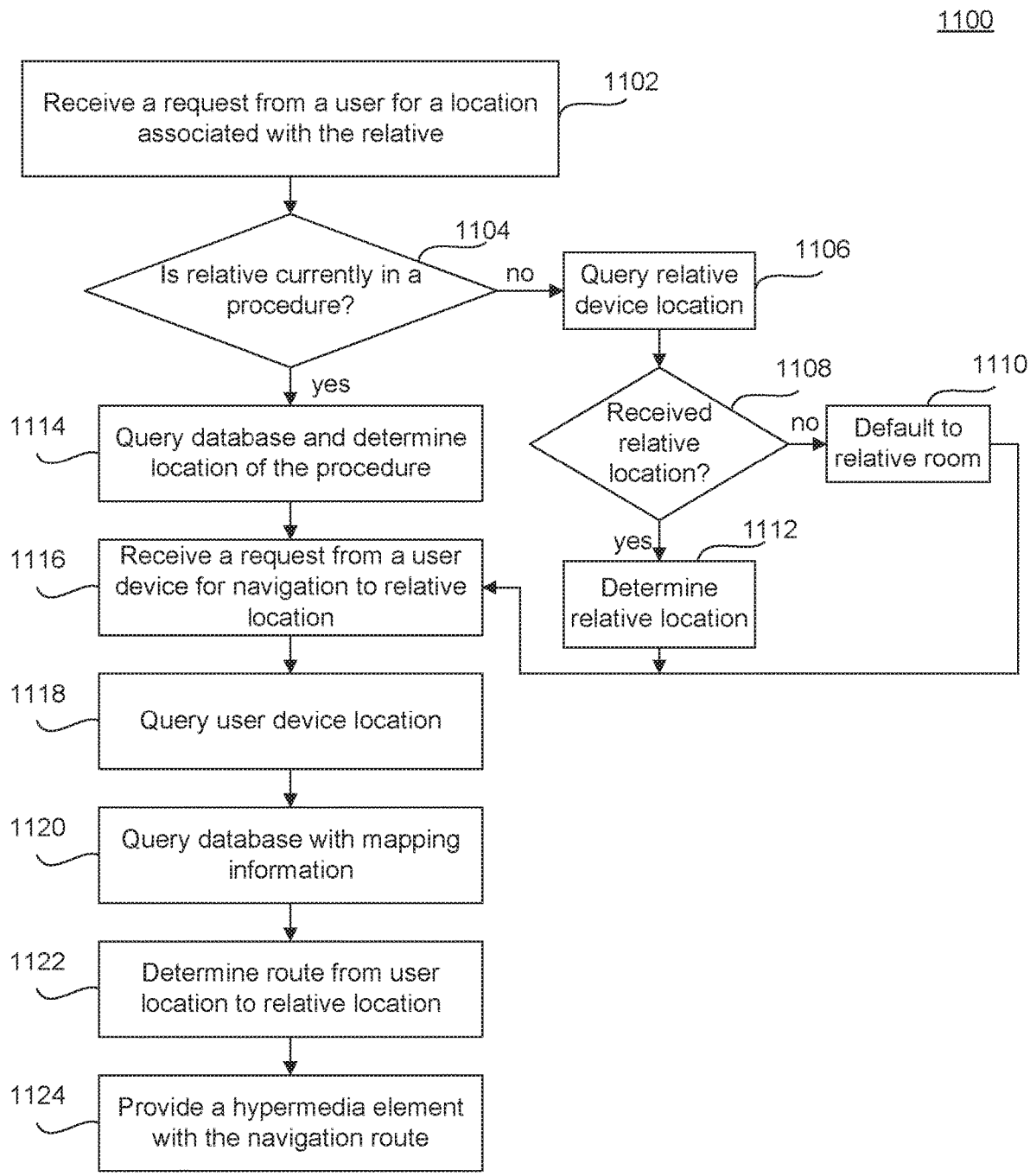
FIG. 11 is a flowchart of an exemplary process for hypermedia elements with navigation instructions.

FIG. 11 is a flowchart of an exemplary process for providing hypermedia elements with navigation instructions. In step 1102, facility server 122 may receive a request from user device 102 for a location associated with relative 105. As a response, in step 1104 facility server 122 may determine if relative 105 is currently in a procedure, based on information collected in step 520.

Facility server 122 may determine that relative 105 is not currently in a service (step 1104: no). Facility server 122 may then proceed to query the location of relative device 103. It may do so by broadcasting a signal to internal location devices 125, querying the chronological list of events associated with relative 105, or accessing location service 190. When a location is received as response from the query (step 1108: yes), facility server 122 may determine the location of relative 105 based on the location of relative device 103. Alternatively, if no location is received from the query (step 1108: no), facility server 122 may determine that relative is at a default location such as relative 105 room.

In step 1104 facility server 122 may also determine that the relative is currently in a procedure (step 1104: yes). In such situation, facility server 122 may query local and/or external databases to determine the location of the procedure currently taken place with relative 105.

Facility server 122 may then automatically generate and provide a hypermedia element to user device 102 with information associated the location of relative 105. In step 1116, as a response, facility server 122 may receive a request for navigation instructions from user device 102. Facility server may then query the location of user device 102 in step 1118, for example by requesting information to location service 190. In step 1120, facility server may query local and external databases for mapping information.

In step 1122, facility server 122 may determine a route from the location of user device 102 to the location of relative 105 previously determined. Facility server 122 may then automatically generate at least one hypermedia element with the route information.

In step 1124, facility server may provide the route associated hypermedia element(s) to user device 102.

Figure 12:
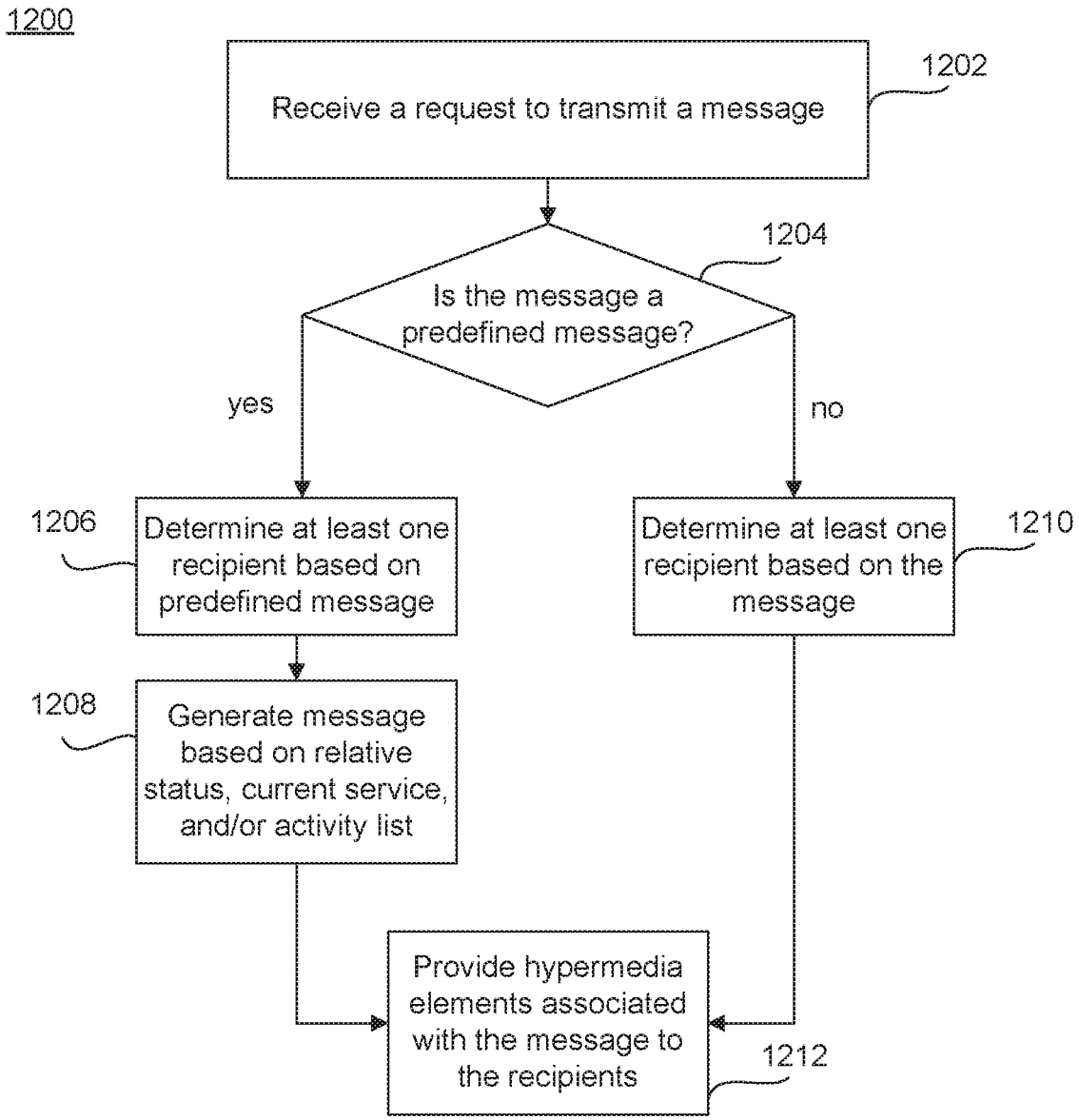
FIG. 12 is a flowchart of an exemplary process for providing hypermedia elements with a message.

FIG. 12 is a flowchart of an exemplary process for providing hypermedia elements with a message. In step 1202, facility server 122 may receive a request to transmit a message. The request may include message information, message sender, and message receiver(s). The message may also include data fields that indicate if the message is predefined. For example, if the message is automatically generated by a program 342 in user device 102, it will have a data field indicating that the message is predefined. In some embodiments, predefined messages may forward the status of relative 105 to all authorized users. In other embodiments, a predefined message may include an invitation to join an activity.

In step 1204, based on the message information and/or variables associated with the message, facility server 122 may determine that the message is a predefined message (step 1204: yes). Facility server 122 may then continue to step 1206 and determine at least one recipient. Facility server 122 may then automatically generate the message based on the status of relative 105, current procedure, and/or the activity list. Alternatively, facility server 122 may determine that the message is not a predefined message (step 1204: no). It may then determine at least one recipient based on the received message information. In step, 1212, facility server may automatically generate hypermedia elements associated with the message and provide the hypermedia elements to the recipient(s).

Figure 13:
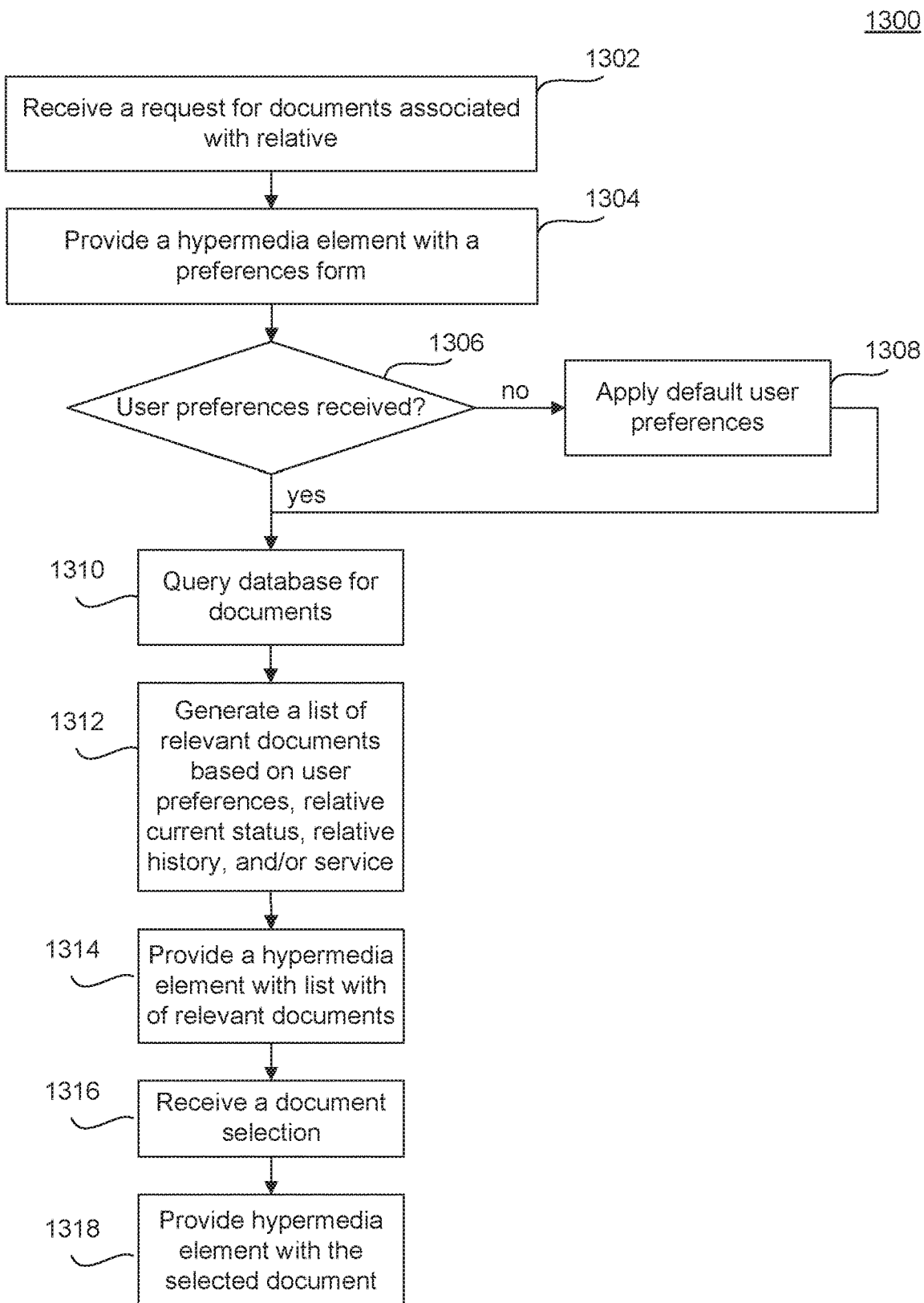
FIG. 13 is a flowchart of an exemplary process for providing hypermedia elements associated with documents.

FIG. 13 is a flowchart of an exemplary process for providing hypermedia elements associated with documents. In step 1302, facility server 122 may receive a request for documents associated with relative 105. These documents may include, for example, health care records of relative 105, literature relevant to the condition of relative 105, and/or information about the facility. As a response, facility server 122 may provide a hypermedia element which includes a preferences form. The form may include categories of documents (like the ones previously described), cost of document preferences, or document length preferences.

In step 1306, facility server 122 may determine if fields in the hypermedia element were filled by user 104. When no user preferences are inputted (step 1306: no), facility server 122 may apply default preferences and continue to step 1310. In step 1310, facility server 122 may query local and/or external databases for documents selected based on relative 105 and/or user preferences.

In step 1312, facility server 122 may automatically generate a list of documents based on user preferences, current status of relative 105, events associated with relative 105, and/or procedures associated with relative 105. Facility server 122 may then automatically generate a single or a plurality of hypermedia elements and provide them to user device 102 in step 1314.

In step 1316, facility server 122 may receive a specific document selection. Facility server 122 may then query databases obtain the specific document, automatically generate a hypermedia element related to the document, and may provide information to display the selected document in user device 102 screen.

Figure 14:
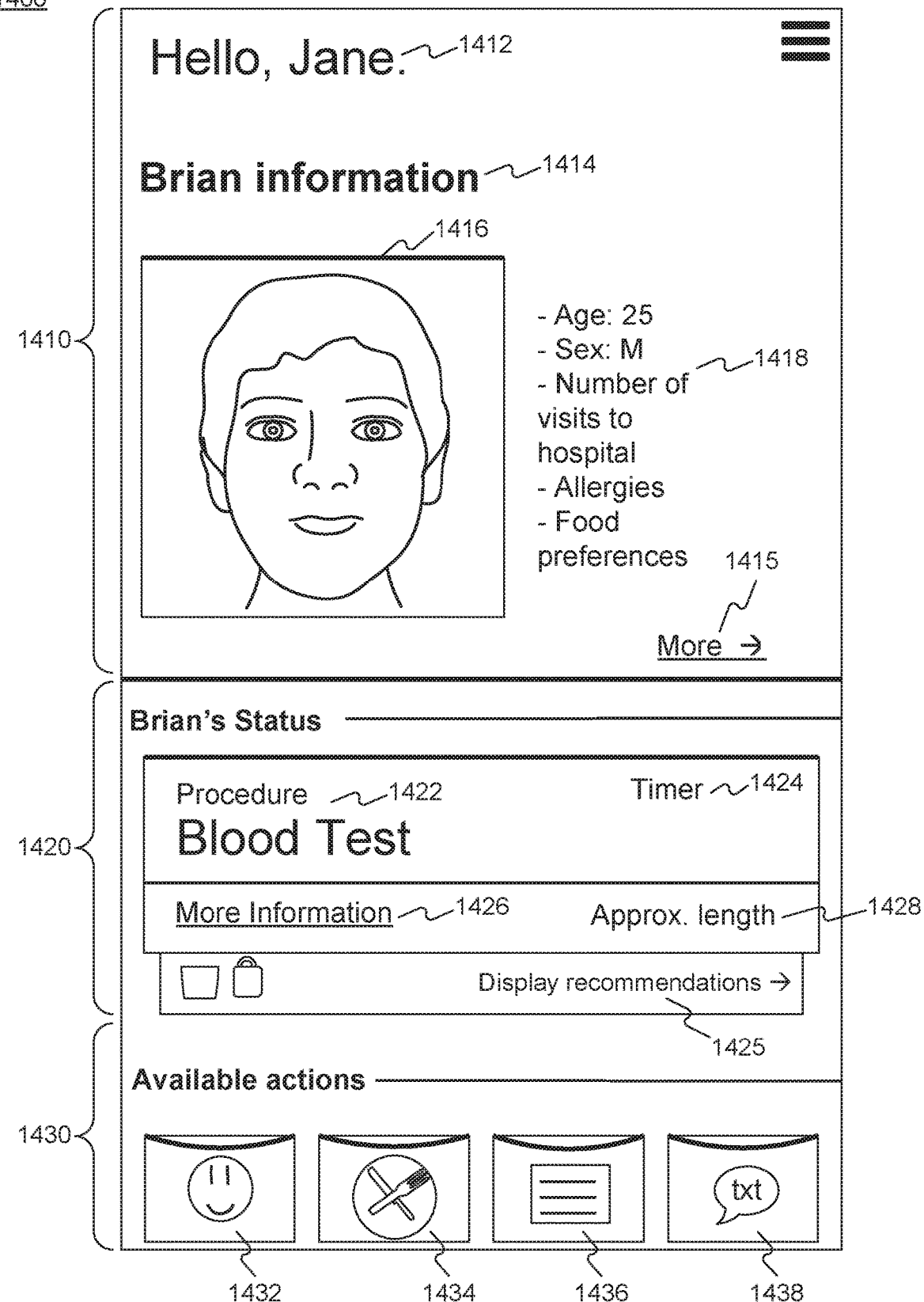
FIG. 14 is an illustration of an example of a primary hypermedia-generated user interface, consistent with embodiments of the present disclosure.

FIG. 14 is an illustration of an example of a primary hypermedia-automatically generated user interface, consistent with embodiments of the present disclosure. User device 102 may display interface 1400 after receiving hypermedia elements provided by facility server 122 in, for example, step 528. After user 104 sends a request for information, facility server 122 may execute process 500 and provide a GUI to processor 330 or provide hypermedia elements required to display the interface.

Interface 1400 may include a number of different data fields related to the primary request. The data fields may include three sections 1410, 1420, and 1430. First, section 1410 may include identification information of relative 105 and user 104. Section 1410 may include welcome message 1412, identification information 1414, relative image 1416, and relative information 1418. Second, section 1420 may include status information associated with relative 105. Section 1420 may include current procedure 1422, timing information 1424, link to additional information 1426, approximated length of procedure 1428, and recommendation 1425. Third, section 1430 may include available actions. Available actions may include hypermedia elements associated with contacts icon 1432, activities icon 1434, literature icon 1436, and messaging icon 1438.

Figure 15:
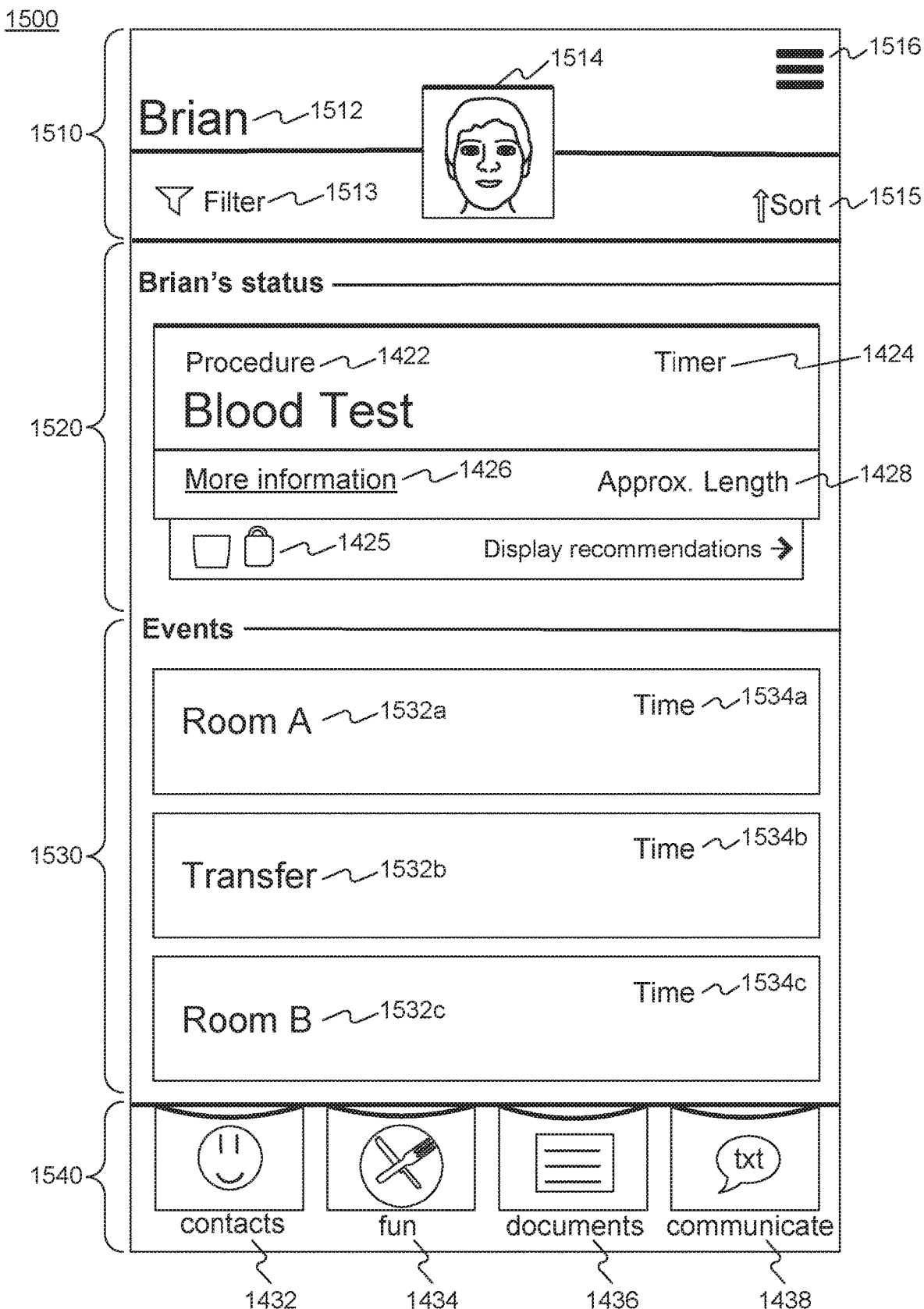
FIG. 15 is an illustration of an example of a secondary hypermedia generated user interface presenting a current status, consistent with embodiments of the present disclosure.

FIG. 15 is an illustration of an example of a secondary hypermedia automatically generated user interface presenting a current status, consistent with embodiments of the present disclosure. Interface 1500 may be provided for example, on the display of user device 102 upon a secondary request for additional information, which may be automatically generated by clicking icon 1415. In other embodiments, the secondary request for additional information may be automatically generated in response to a received input indicative of clicking on relative image 1416 and/or identification information 1414, which may lead to the generation of interface 1500. In some embodiments, interface 1500 may be provided in response to an input indicative of user 104 swiping on certain elements of interface 1400. For example, vertical, horizontal, or diagonal finger movement inputs on interface 1400 may automatically generate a secondary request for additional information.

Interface 1500 may be composed of four sections 1510, 1520, 1530, and 1540. Top section 1510 may include identifier 1512, filter icon 1513, relative image 1514 (which may be a smaller version of 1416), menu icon 1516, and sorting icon 1515. Section 1520 may replicate information in section 1420, and also present current procedure 1422, timing information 1424, link to additional information 1426, approximated length of procedure 1428, and recommendation 1425.

Section 1530 may include a list of events represented in a single or a plurality of hypermedia elements. These objects may be automatically generated in step 808 and may include description 1532, time stamp 1534, and other notes (not shown). Section 1540 in interface 1500 may replicate section 1430, also including contacts icon 1432, activities icon 1434, literature 1436, and messaging 1438.

Figure 16:
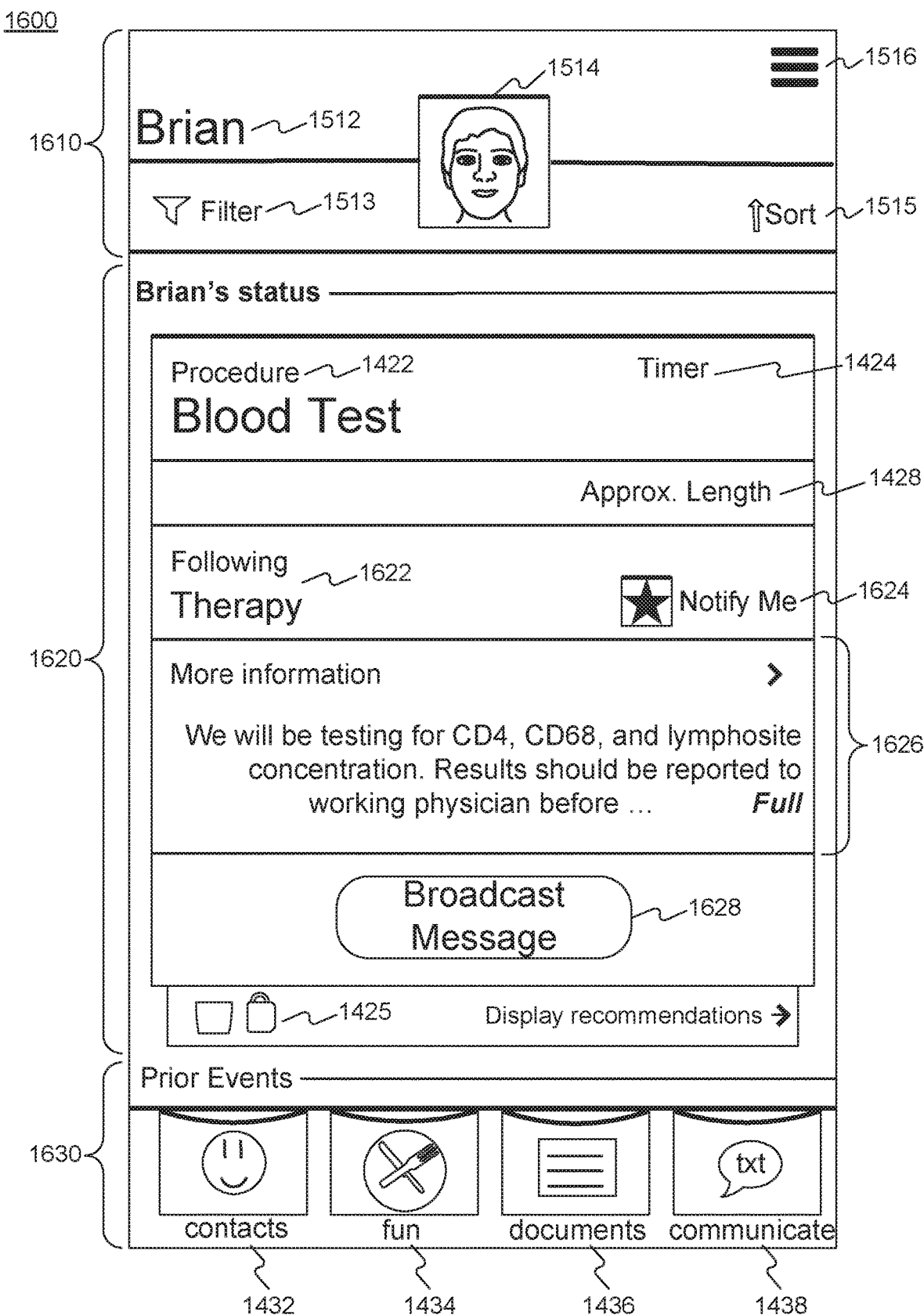
FIG. 16 is an illustration of an example of a secondary hypermedia-based GUI presenting information associated with a procedure, consistent with embodiments of the present disclosure.

FIG. 16 is an illustration of an example of a secondary hypermedia-based GUI presenting information associated with a procedure, consistent with embodiments of the present disclosure. Processor 330 may display interface 1600 after receiving a GUI from facility server 122 or after receiving hypermedia elements with information associated with a procedure of relative 105. For example, facility server 122 may provide a GUI or hypermedia elements that include information associated with a procedure in step 718 to processor 330.

Interface 1600 may include sections 1610, 1620, and 1630. Sections 1610 and 1630 may replicate formerly described sections 1510 and 1430 respectively. Section 1620 may include hypermedia elements displayed in the primary interface such as procedure 1422, timer 1424, length of procedure 1428, and recommendations 1425. Additionally, section 1620 may include next procedures 1622, notification icon 1624, more information 1626, and broadcast message icon 1628.

Figure 17:
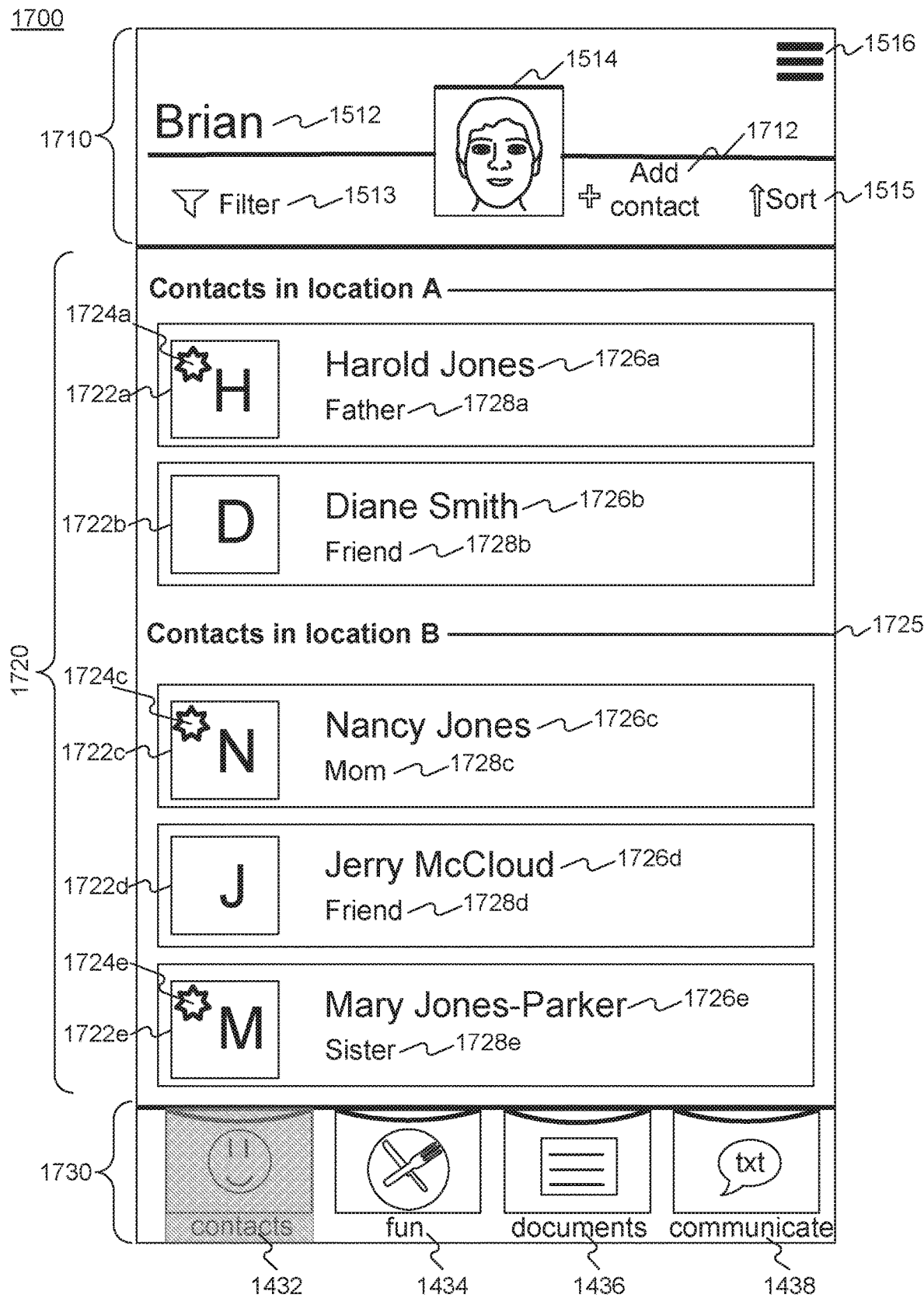
FIG. 17 is an illustration of an example of a secondary hypermedia-based GUI with authorized contacts.

FIG. 17 is an illustration of an example of a secondary hypermedia-based GUI with authorized contacts. Processor 330 may display interface 1700 in user device 102 after receiving a GUI from facility server 122 or after receiving hypermedia elements associated with authorized users. For example, facility server 122 may provide a GUI or hypermedia elements that include information associated with authorized users in step 912 to processor 330.

Interface 1700 may include sections 1710, 1720, and 1730. Sections 1710 and 1730 may replicate formerly described sections 1510 and 1430 respectively. Section 1720 may include a plurality of hypermedia elements associated with authorized users. Each hypermedia element may include an identification icon 1722, preference icon 1724, name 1726, and relationship 1728. Section 1720 may also include subtitles 1725 which represent a list categorization.

The categorization may represent, for example, user location as described in step 910, or may represent a relationship status.

Icons in section 1730 of interface 1700 may have indicators of selection. For example, FIG. 17 shows contacts icon 1432 shaded. In some embodiments, shaded icons may indicate the current location and/or action being displayed. For example specific interfaces may be displayed with the selection of icons 1432, 1434, 1436, and 1438. The selected icon may remain shaded while the associated interface is displayed, indicating user 104 the displayed section. In other embodiments, shaded icons may indicate that user 104 has sent a request to facility server 122 by pressing the icon. For example, indicators of selection may reflect that a call to the server was made by user 104. In yet other embodiments, shaded icons may indicate user 104's most recent selection indicated in a processor log or by a timestamp.

Figure 18:
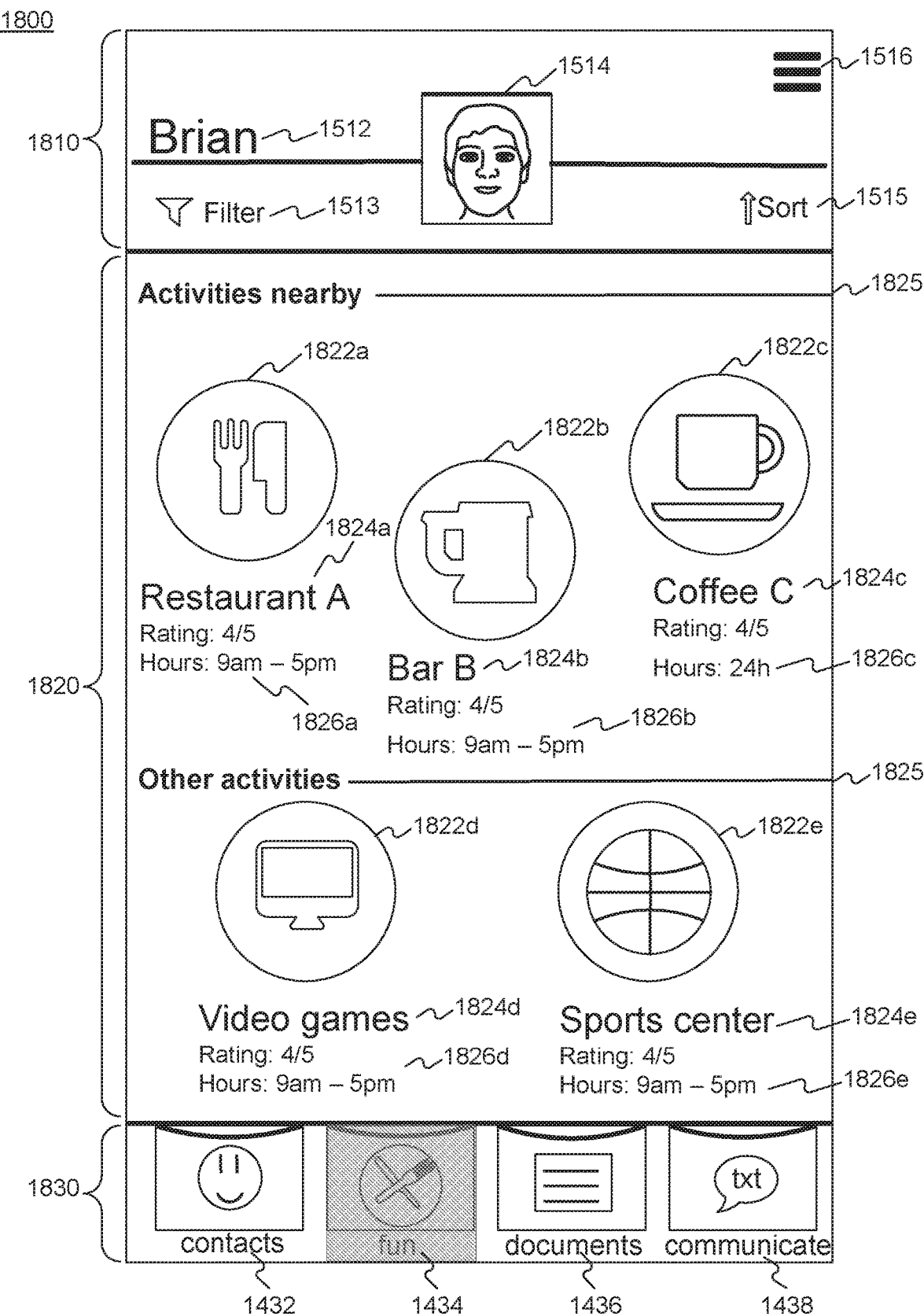
FIG. 18 is an illustration of an example of a secondary hypermedia-based GUI with activities.

FIG. 18 is an illustration of an example of a secondary hypermedia-based GUI with activities. Processor 330 may display interface 1800 in user device 102 after receiving a GUI from facility server 122 or after receiving hypermedia elements associated with authorized users. For example, facility server 122 may provide a GUI or hypermedia elements that include information associated with activities in step 1010 to processor 330.

Interface 1800 may include sections 1810, 1820, and 1830. Sections 1810 and 1830 may replicate formerly described sections 1510 and 1430 respectively. Section 1820 may include a plurality of hypermedia elements associated with activities. Each hypermedia element may include an identification icon 1822, activity identification 1824, and associated information 1826. Section 1820 may also include subtitles 1825 which represent categorizations based on type of activity, or a recommendation automatically generated in a process like the one described in step 1018.

Icons in section 1830 of interface 1700 may have indicators of selection. For example, FIG. 18 shows activities icon 1434 shaded. In some embodiments, shaded icons may indicate the current location and/or action being displayed. In other embodiments shaded icons may indicate user's 104 last selection. In yet other embodiments, shaded icons may indicate that user 104 has sent a request to facility server 122 by pressing a selected icon This is indicating that user 104 has sent a request to facility server 122 by pressing the icon.

Figure 19:
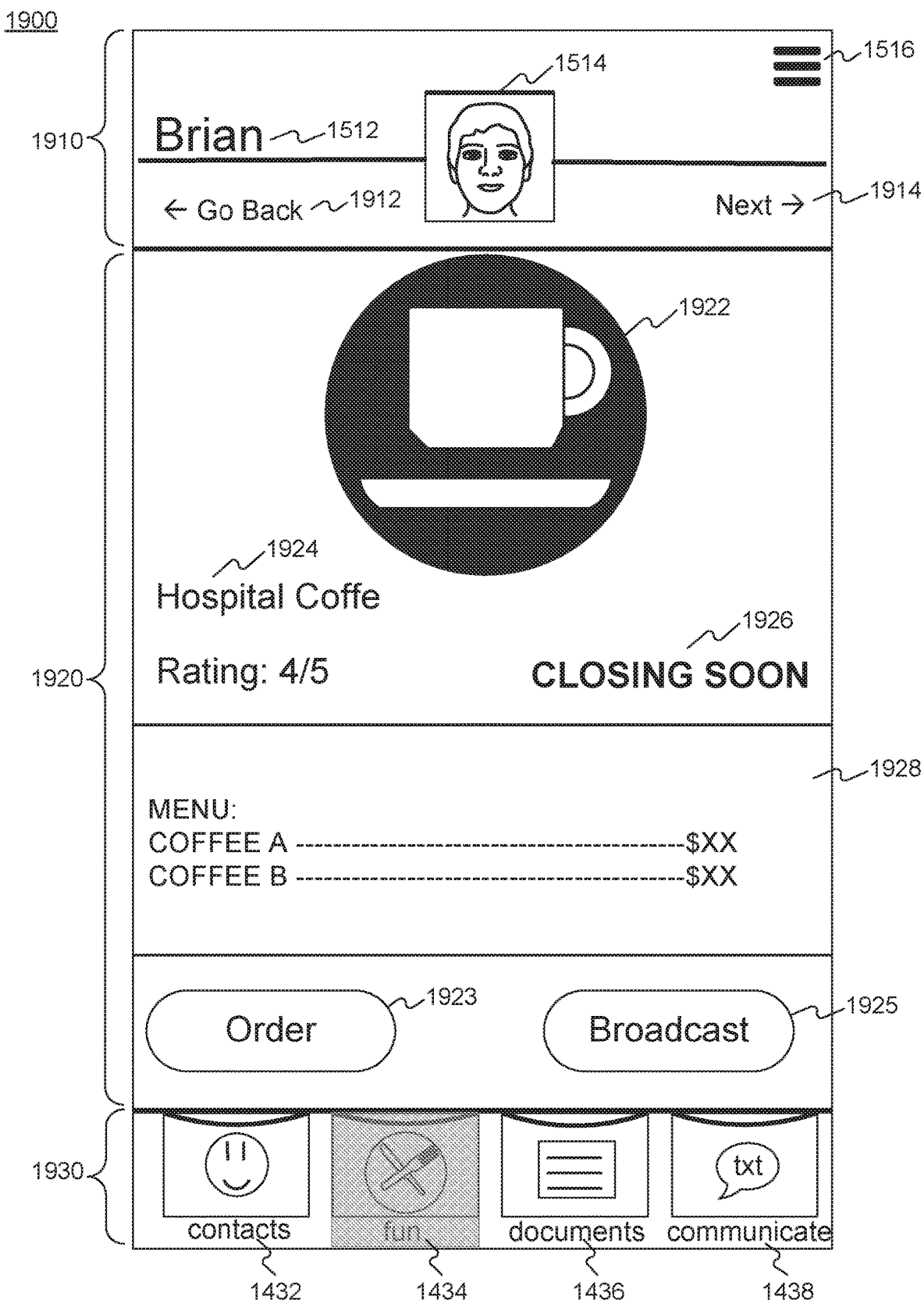
FIG. 19 is an illustration of an example of a secondary hypermedia-based GUI with activities information.

FIG. 19 is an illustration of an example of a secondary hypermedia-based GUI with activities information. Processor 330 may display interface 1900 in user device 102 after receiving a GUI from facility server 122 or hypermedia elements associated with an activity.

Interface 1900 may include sections 1910, 1920, and 1930. First, in addition previously displayed hypermedia elements such as identifier 1512, filter icon 1513, relative image 1514, menu icon 1516, and sorting icon 1515, section 1910 may also display reverse icon 1912 and forward icon 1914 for navigation within the program. Second, section 1920 may include activity icon 1922 (representing a selected activity), activity identification 1924, activity details 1926, activity information 1928, ordering icon 1923, and broadcasting icon 1925. Third, section 1930 may replicate section 1430 but sustain the indicators of selection.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware, firmware, and software, but systems and methods consistent with the present disclosure can be implemented as hardware alone.

Computer programs based on the written description and methods of this specification are within the skill of a software developer. The various programs or program modules can be created using a variety of programming techniques. For example, program sections or program modules can be designed in or by means of Java, C, C++, assembly language, or any such programming languages. One or more of such software sections or modules can be integrated into a computer system, non-transitory computer-readable media, or existing communications software.

Moreover, while illustrative embodiments have been described herein, the scope includes any and all embodiments having equivalent elements, modifications, omissions, combinations (e.g., of aspects across various embodiments), adaptations or alterations based on the present disclosure. Further, the steps of the disclosed methods can be modified in any manner, including by reordering steps or inserting or deleting steps.

The invention claimed is:

1. A method for providing hypermedia elements to generate a graphical user interface, the method comprising:
receiving, from a user device at a facility server of a facility, a request to generate the graphical user interface related to a relative of a user of the user device, the relative being located within the facility, wherein the request comprises an identifier of the relative;
determining the user is an authorized user;
generating, responsive to determining the user is an authorized user, a hypermedia icon comprising an image of the relative, wherein the generating is responsive to receiving a response from an indexing service to a query for the image of the relative transmitted to the indexing service;
generating at least one hypermedia element corresponding to a current status of the relative indicating the relative is undergoing a procedure, wherein the generating is responsive to receiving a response to a query communicated from the facility server to one or more components within a system of the facility;
generating at least one action hypermedia element representing actions that can be executed by the user, wherein in response to the user interacting with one of the at least one action hypermedia elements the facility server receives a query corresponding to the one of the at least one action hypermedia elements, wherein the at least one action hypermedia elements comprise an element for a list of activities within a predetermined proximity of the user device; and
generating a recommendation based upon a duration of the procedure.

2. The method of claim 1, wherein the determining comprises comparing identification information of the user device with a list of authorized users.

3. The method of claim 1, wherein the determining comprises providing instructions to the user device to generate a hypermedia form that captures authentication information and receiving the authentication information at the facility server.

4. The method of claim 3, wherein the authentication information comprises a password provided by the user within the hypermedia form.

5. The method of claim 1, wherein the determining comprises sending a request to a device of the relative to authorize the user device.

6. The method of claim 1, wherein the current status comprises at least one of: location, personal information, doctors' notes, scheduled procedures, and scheduled services.

7. The method of claim 1, wherein the one or more components comprises a device of the relative.

8. The method of claim 1, wherein the at least one action hypermedia element comprises an element for accessing documents of the relative.

9. A system for providing hypermedia elements to generate a graphical user interface, the system comprising:
a facility server comprising a processor and a memory device that stores instructions executable by the processor, wherein the instructions comprise instructions that:
receive, from a user device at the facility server of a facility, a request to generate the graphical user interface related to a relative of a user of the user device, the relative being located within the facility, wherein the request comprises an identifier of the relative;
determine the user is an authorized user;
generate, responsive to determining the user is an authorized user, a hypermedia icon comprising an image of the relative, wherein the generating is responsive to receiving a response from an indexing service to a query for the image of the relative transmitted to the indexing service;
generate at least one hypermedia element corresponding to a current status of the relative indicating the relative is undergoing a procedure, wherein the generating is responsive to receiving a response to a query communicated from the facility server to one or more components within a system of the facility;
generate at least one action hypermedia element representing actions that can be executed by the user, wherein in response to the user interacting with one of the at least one action hypermedia elements the facility server receives a query corresponding to the one of the at least one action hypermedia elements, wherein the at least one action hypermedia elements comprise an element for a list of activities within a predetermined proximity of the user device; and
generate a recommendation based upon a duration of the procedure.

10. The system of claim 9, wherein the determining comprises comparing identification information of the user device with a list of authorized users.

11. The system of claim 9, wherein the determining comprises providing instructions to the user device to generate a hypermedia form that captures authentication information and receiving the authentication information at the facility server.

12. The system of claim 11, wherein the authentication information comprises a password provided by the user within the hypermedia form.

13. The system of claim 9, wherein the determining comprises sending a request to a device of the relative to authorize the user device.

14. The system of claim 9, wherein the current status comprises at least one of: location, personal information, doctors' notes, scheduled procedures, and scheduled services.

15. The system of claim 9, wherein the one or more components comprises a device of the relative.

16. The system of claim 9, wherein the at least one action hypermedia element comprises an element for accessing documents of the relative.

17. A product for providing hypermedia elements to generate a graphical user interface, the product comprising:
a non-transitory storage device that stores code, the code being executable by a processor and comprising:
code that receives, from a user device at a facility server of a facility, a request to generate the graphical user interface related to a relative of a user of the user device, the relative being located within the facility, wherein the request comprises an identifier of the relative;
code that determines the user is an authorized user;
code that generates, responsive to determining the user is an authorized user, a hypermedia icon comprising an image of the relative, wherein the generating is responsive to receiving a response from an indexing service to a query for the image of the relative transmitted to the indexing service;
code that generates at least one hypermedia element corresponding to a current status of the relative indicating the relative is undergoing a procedure, wherein the generating is responsive to receiving a response to a query communicated from the facility server to one or more components within a system of the facility;
code that generates at least one action hypermedia element representing actions that can be executed by the user, wherein in response to the user interacting with one of the at least one action hypermedia elements the facility server receives a query corresponding to the one of the at least one action hypermedia elements, wherein the at least one action hypermedia elements comprise an element for a list of activities within a predetermined proximity of the user device; and
code that generates a recommendation based upon a duration of the procedure.

* * * * *